United States Patent
Janik et al.

(10) Patent No.: US 10,046,158 B2
(45) Date of Patent: Aug. 14, 2018

(54) IMPLANTABLE ELECTRODE ARRAY ASSEMBLY WITH AN ARRAY SUBSTRATE, ELECTRODES AND INTEGRATED CIRCUITS, THE INTEGRATED CIRCUITS BEING ATTACHED TO PACKAGE SUBSTRATES

(75) Inventors: John Janik, Hudsonville, MI (US); Rob Brindley, Delton, MI (US); Edward Chia-Ning Tang, Ann Arbor, MI (US); James Bernard Dunlop, Jr., Colorado Springs, CO (US); Leland Joseph Spangler, Manitou Springs, CO (US)

(73) Assignee: STRYKER CORPORATION, Kalamazoo, MI (US)

( * ) Notice: Subject to any disclaimer, the term of this patent is extended or adjusted under 35 U.S.C. 154(b) by 599 days.

(21) Appl. No.: 13/491,777

(22) Filed: Jun. 8, 2012

(65) Prior Publication Data
US 2012/0330393 A1 Dec. 27, 2012

Related U.S. Application Data

(63) Continuation of application No. PCT/US2010/059691, filed on Dec. 9, 2010.
(Continued)

(51) Int. Cl.
*A61N 1/04* (2006.01)
*A61N 1/05* (2006.01)
(Continued)

(52) U.S. Cl.
CPC .......... *A61N 1/0551* (2013.01); *A61N 1/0553* (2013.01); *H01L 23/3121* (2013.01); *H01L 23/5387* (2013.01); *H01L 2924/0002* (2013.01)

(58) Field of Classification Search
CPC ...... A61N 1/04; A61N 1/0551; A61N 1/0553; H01L 23/3121; H01L 23/5387; H01L 2924/0002; H01L 2924/00
(Continued)

(56) References Cited

U.S. PATENT DOCUMENTS 4,969,468 A * 11/1990 Byers et al. .................. 600/373
7,308,317 B1 12/2007 Okandan et al.
(Continued)

FOREIGN PATENT DOCUMENTS

EP 1 883 107 A2 1/2008

OTHER PUBLICATIONS

PCT/US2010/059691 "International Search Report and Written Opinion", dated Apr. 27, 2011.

*Primary Examiner* — Carl H Layno
*Assistant Examiner* — Jon Eric C Morales
(74) *Attorney, Agent, or Firm* — Howard & Howard Attorneys PLLC

(57) ABSTRACT

An electrode array with a flexible array substrate on which plural spaced apart electrodes are disposed. Integrated circuits are disposed in the array substrate. The integrated circuits are mounted to package substrates. The package substrates are more rigid than the array substrate. Internal to each package substrate is at least one electrical conductor. The electrical conductor extends from a bond pad integral with integrated circuit at least partially through the package substrate. The electrical conductor functions as the conductive member that extends between the integrated circuit an electrode with which the integrated circuit is associated.

24 Claims, 14 Drawing Sheets

Related U.S. Application Data

(60) Provisional application No. 61/285,827, filed on Dec. 11, 2009.

(51) Int. Cl.
  *H01L 23/31* (2006.01)
  *H01L 23/538* (2006.01)

(58) Field of Classification Search
  USPC .......................................... 607/148; 600/373
  See application file for complete search history.

(56) References Cited

U.S. PATENT DOCUMENTS

| | | |
|---|---|---|
| 2007/0207569 A1* | 9/2007 | Greenberg et al. ........... 438/106 |
| 2011/0034977 A1 | 2/2011 | Janik et al. |
| 2011/0077660 A1 | 3/2011 | Janik et al. |
| 2012/0022551 A1 | 1/2012 | Staunton et al. |

* cited by examiner

IMPLANTABLE ELECTRODE ARRAY ASSEMBLY WITH AN ARRAY SUBSTRATE, ELECTRODES AND INTEGRATED CIRCUITS, THE INTEGRATED CIRCUITS BEING ATTACHED TO PACKAGE SUBSTRATES

RELATIONSHIPS TO EARLIER FILED APPLICATIONS

This application is a continuation of PCT App. No. PCT/US2010/059691 filed 9 Dec. 2010. PCT App. No. PCT/US2010/059691 is a non-provisional of U.S. Provisional Pat. App. No. 61/285,827 filed 11 Dec. 2009. This application incorporated by reference the above-identified applications from which this application now claims priority.

FIELD OF THE INVENTION

This invention relates generally to an implantable electrode array assembly and, more particularly, to an implantable electrode array with a number of individually activated electrodes wherein each electrode is integral with the semiconductor chip that sources current to/sinks current from the electrode.

BACKGROUND OF THE INVENTION

There are a number of medical conditions for which it has been found that an effective therapy involves driving current through a section of the tissue of a patient. Often, the current is driven between the electrodes of an electrode array implanted in the patient. Generally, the electrode array includes a non-conductive carrier on which typically two or more electrodes are disposed. Once the electrode array is implanted, current is driven from at least one of the electrodes, through the adjacent tissue, to at least one of the other electrodes. The current flow through the tissue influences the tissue to accomplish a desired therapeutic result. For example, an electrode array positioned adjacent the heart may flow currents to stimulate the appropriate contraction and expansion of the heart muscles.

There is an increasing interest in implanting electrode arrays adjacent neural tissue so that the resultant current flow induces a desired neurological or physical effect. In one known application, the current driven between the electrodes of an array placed on top of the dura in the vertebral column reduces the extent to which chronic pain signals are perceived by the brain. Alternatively, the array may be placed in a location where the current flow stimulates a feeling of satiation as part of an appetite suppression/weight management therapy. In another application, the current is flowed to tissue or nerves associated with the bladder or the anal sphincter to assist in control of incontinence. Electrodes may be implanted in a paralysis victim to provide muscle control and/or a sense of feeling.

The Applicants' Patent Application Nos. No. PCT/US2009/33769, FOLDABLE, IMPLANTABLE ELECTRODE ARRAY ASSEMBLY AND TOOL FOR IMPLANTING SAME, filed 11 Feb. 2009, published as WO 2009/111142 and US Pat. Pub. No. 2011/0077660, and U.S. patent application Ser. No. 12/535,717, IMPLANTABLE ELECTRODE ARRAY ASSEMBLY INCLUDING A CARRIER FOR SUPPORTING THE ELECTRODES AND CONTROL MODULES FOR REGULATING OPERATION OF THE ELECTRODES EMBEDDED IN THE CARRIER, AND METHOD OF MAKING SAME, filed 5 Aug. 2009 the contents of which are published in US Pat. Pub. No. 2011/0034977 A1, the contents of which are explicitly incorporated herein by reference, each describe electrode array that includes a carrier on which plural electrodes are arranged in a row by column matrix. An advantage of this electrode array is that it allows current to be flowed between numerous different combinations of electrodes. Depending on which electrodes are connected to associated current sources and sinks, this array can be operated so that there are two or more current flows occurring simultaneously between different sets of electrodes. Once this assembly is deployed, the practitioner can initially drive current between different combinations of electrodes. Current therefore flows through different sections of tissue. This allows the practitioner to determine between which electrodes, through which tissue, the current flow offers the greatest benefit and/or tolerable side effects. Once the optimal current flow path between the electrodes is determined, the array and its associated power supply are set to operate in this state.

In comparison to other electrode arrays with lesser numbers of electrodes, the above-described array makes it possible to flow current through more sections of tissue and to selectively focus/diffuse the current flow. In contrast to an electrode array with a smaller number of electrodes, use of the above-described array increases the likelihood that the current flow can be set to provide desired therapeutic effects, with tolerable side effects.

Still another advantage of the above-described array is that the carrier is formed from superelastic material. A superelastic material is one that, after being subjected to appreciable bending or folding, returns to its initial state. Thus, once this electrode array is formed, the assembly is then folded or rolled into a form that has a side-to-side width appreciably less than its width in the unfolded/unrolled state. A benefit of an electrode array assembly of this design is that it can be folded into a sheath. The sheath-encased electrode array assembly can then be inserted through an access cannula using a minimally invasive procedure into the patient. Once in the patient, the sheath and assembly are steered to over the tissue against which the electrodes integral with the assembly are deployed. Once the assembly is properly positioned, the sheath is opened up or removed. The opening/removal of the sheath causes the carrier to unfold. As a consequence of the carrier unfolding, the electrodes deploy over the target tissue. A more complete understanding of how the electrode array assembly can be so positioned and deployed is contained in the Applicants' Assignee's U.S. Pat. App. No. 61/166,366, DELIVERY ASSEMBLY FOR PERCUTANEOUSLY DELIVERING AN ELECTRODE ARRAY AT A TARGET LOCATION, THE ASSEMBLY CAPABLE OF STEERING THE ELECTRODE ARRAY TO THE TARGET LOCATION, filed 3 Apr. 2009, which is incorporated herein by reference the contents of which are published in WO 2010/114998 A1/US Pat. Pub. No. US 2012/0022551 A1.

Application Ser. No. 12/535,717 further describes how each electrode may be built over the control module that currents the components that source current to/sink current from the electrode. An advantage of this arrangement is that it eliminates that need to, from a central location, run a large number of conductors from the current source/sink components to the individual electrodes. Instead, a single bus, or a bus is connected to each of the control modules. Instructions transmitted over the bus inform each control module if it should, serve as a current source, be turned off, or serve as a current sink. Since there are relatively few bus conductors, these conductors can be relatively large in size. This reduces the fragility of these conductors. Further the conductors that extend from each control module to the associated electrode are relatively short in length. Also, the electrode array of this invention is further constructed so that the conductors that extend to the electrodes are oriented on axes perpendicular to the plane of the electrode array assembly. The electrode array assembly is exposed to relatively minimal stress along the axes perpendicular to these conductors. Collectively, these design features serves to reduce the stress to which these control module-to-electrode conductors are exposed and therefore, the possibility that they can break.

While the Applicants' previous inventions offer improvements over other electrode array assemblies, there are some disadvantages associated with them. Some of these disadvantages are associated with the manufacture of the array. This invention requires that openings be formed in the carriers. These openings define the void spaces in which the control modules are seated. In order to ensure that the modules do not shift position in the openings, it is necessary that they be precisely dimensioned relative to the other components of the array. There are concerns that the manufacturing processes needed to so fabricate the openings to ensure these openings are precisely sized may significantly add to the cost of fabricating the array,

SUMMARY OF THE INVENTION

This invention is related to a new and useful electrode array designed for implantation into a living being. The electrode array of this invention includes at least one or more electrode ASIC packages (EAPs). Each EAP consists of an integrated circuit that includes components for sourcing and/or sinking current. The circuit is contained in a package. Disposed over an outer surface of the package are one or more conductors. These conductors function as the electrodes of the EAP.

In many versions of the invention, the EAPs are disposed on an array substrate. Also disposed on the array substrate, often between the body of the substrate and the EAPs are one or more conductors. These conductors collectively form the bus over which power is distributed to the EAPs, instructions are broadcast to the EAPs and data regarding the operation of the EAPs are transmitted.

Also in many versions of the invention, each EAP includes a package substrate. Typically, the package substrates are more rigid than the array substrate. The EAP is constructed so that the on package electrode (electrodes) and the package substrate are located over opposed faces of the integrated circuit. Conductors internal to the package substrate extend to bond pads on the integrated circuit. Often, at least one of these conductors is used to establish an electrical connection between the integrated circuit and the overlying electrode.

The electrode array of this invention often includes a frame. The frame is formed out of material that provides the array with at a minimum, some structural rigidity. In some versions of the invention, the frame is formed out of material that is flexible. In some versions of the invention, the frame is formed out of superelastic material. Often, the frame is disposed over the substrate. The frame typically has structural components that at least partially surround the EAPs. A shell formed from flexible, electrically insulating material is disposed around the partially assembly array. More particularly, the insulating material forming the shell is disposed around the underside and sides over the substrate, over the frame and between the EAPs and the frame. The insulting material forming the shell thus holds the components forming the electrode array assembly together. This insulating material also functions as an insulating layer between the EAPs and the frame.

In many versions of this invention, the array also includes a transfer package. The transfer package includes components that function as the interface between the external conductors over which power and instructions are supplied to the array and the on-substrate bus. The transfer package may be attached to the array using the same means and at the same time the EAPs are secured to the array.

The EAPs of the array of this invention are constructed so that the conductors that extend from the components internal to the integrated circuit to the associated electrode, as well as the electrode, are rigidly bonded to the circuit. There is no movement of these components relative to each other. This serves to eliminate the possibility that such movement could stress the conductors to the point at which they fracture.

Still another feature of the electrode array of this invention is that while the structure components of the frame may need to extend around the EAPs, there is no requirement that these components be in a precise distance from each other. This serves to reduce the cost associated with both providing the frame and bonding the frame to the rest of the array.

BRIEF DESCRIPTION OF THE DRAWINGS

The invention is pointed out with particularity in the claims. The above and further features and advantages of this invention are understood by following Detailed Description taken in conjunction with the accompanying drawings in which

DETAILED DESCRIPTION

I. First Embodiment

Figure 1:
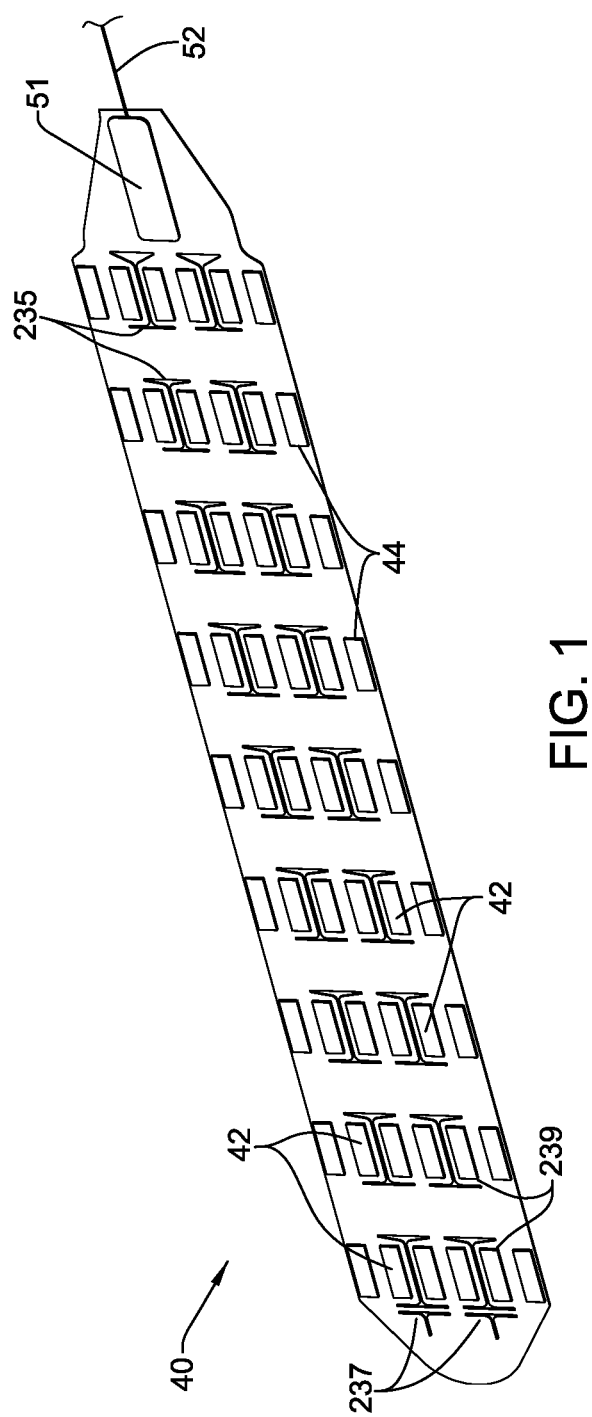
FIG. 1 is a perspective view of an electrode array constructed in accordance with this invention.
Figure 2:
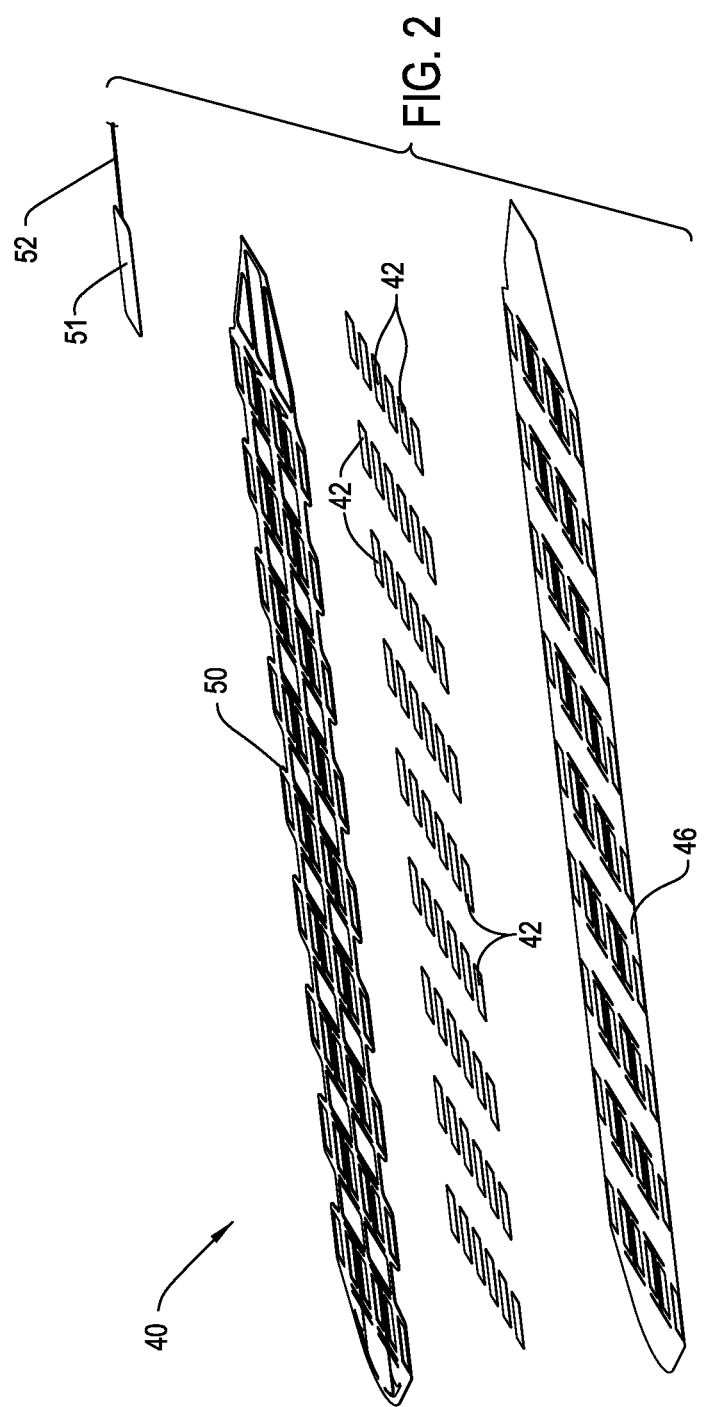
FIG. 2 is an exploded view of the electrode array of FIG. 1.
Figure 3:
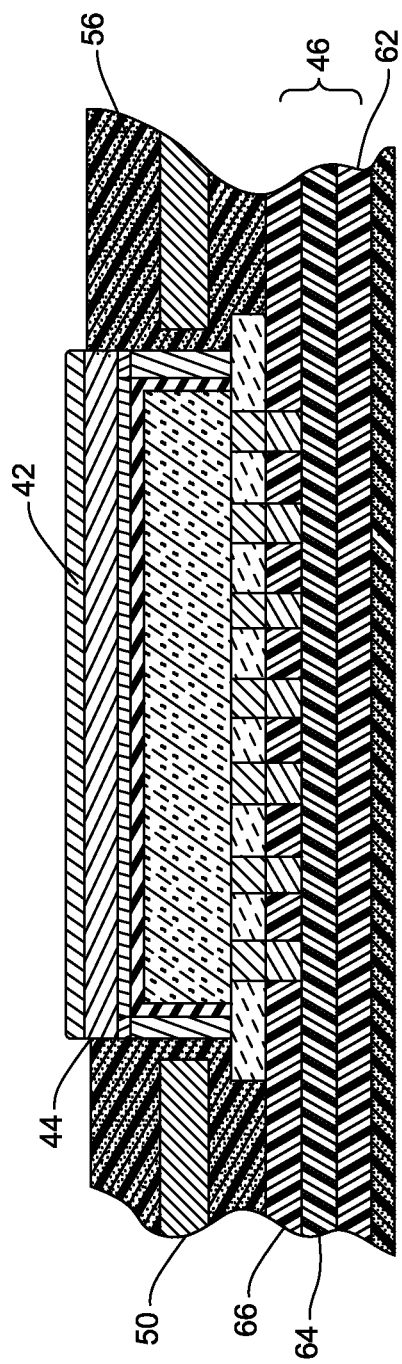
FIG. 3 is a cross sectional view of the electrode array of FIG. 1.

FIGS. 1, 2 and 3 illustrate the basic features of an electrode array 40 constructed in accordance with this invention. Array 40 includes a number of spaced apart electrodes 42. In the illustrated version of the invention, the electrodes 42 are arranged in a row by column pattern. In most versions of the invention, there are at least 10 electrodes 42, in many versions of the invention there are 20 or more electrodes and, often, 40 or more electrodes. Each electrode 42 is part of an electrode ASIC package 44, (EAP). Each EAP 44, in addition to having an electrode 42, includes components, seen in FIG. 10, that source or sink current to the electrode. These components may also monitor the voltage present at the associated electrode 42.

The EAPs 44 are disposed on a non-conductive substrate 46. A multi-conductor bus 48 (FIG. 7) internal to the substrate 46 supplies power and operating instructions the EAPs 44. A frame 50, like EAPs 44, is disposed on the substrate. Frame 50 is formed of material that provides some rigidity to the array 40. Typically the material from which the frame 50 is formed has some flexibility though less than that of the substrate 46. Frame 50 includes structural components that at least partially surround the EAPs 44.

A transfer package 51 is mounted to one end of the array 40. In FIGS. 1 and 2, the transfer package 51 is shown at the right end of the array 40, arbitrarily, the "proximal" end of the array 40. The left end of the array is the "distal" end of the array. Transfer package 51 contains the components that function as an interface that extends between the conductors 52 external to the array 40 and the conductors forming bus 48. Conductors 52, shown as a single cable in the Figures, extend to an implantable device controller. The implantable device controller, which is not illustrated, is the implantable unit that provides the power for the current sources and sinks internal to the EAPs 44 as well as the instructions that indicated to which electrodes 42 the current should be source or sunk. The specific structure of the implantable device controller is not part of this invention.

Electrode array 40 of this invention also includes a shell 56 formed from, flexible, biocompatible electrically insulating material such as liquid crystal polymer or parylene. Shell 56 extends over the exposed surfaces of substrate 46, frame 50 and transfer package 51. The material forming shell 56 is also disposed between the EAPs 44 and the frame 50. Shell 56 does not extend over the whole of the EAPs 44. Instead, the top portions of the EAPs 44, the portions on which the electrodes 42 are disposed, extend above the outer surface of the shell 56. Thus, when electrode array 40 is disposed against tissue through which current is to be flowed, the electrodes 42 are in contact with the tissue.

Figure 4:
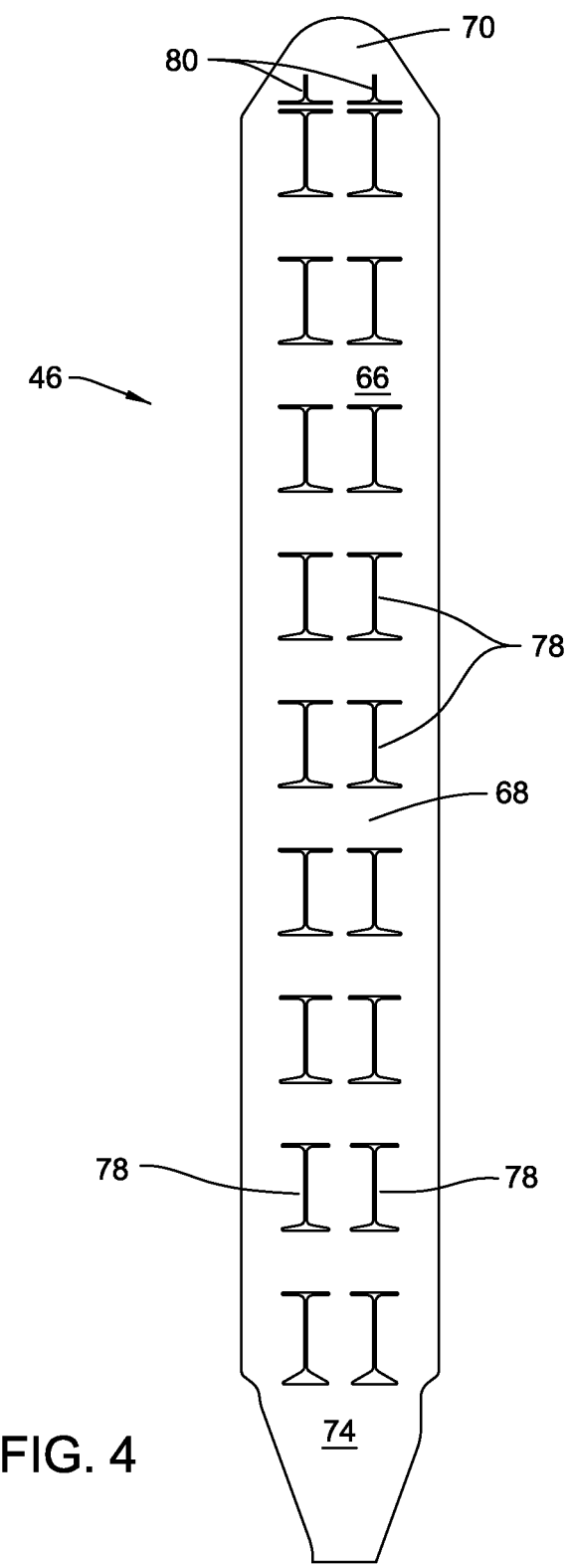
FIG. 4 is a plan view of the top of the substrate.

Substrate 46, sometimes referred to as the array substrate, is now described initially with respect to FIGS. 3 and 4, is a laminate structure. In the illustrated version of the invention substrate 46 is formed from three layers of electrically insulating material so as to have a bottom layer 62, a middle layer 64 and an upper layer 66. Layers 62, 64 and 66 may be formed from material such as liquid crystal polymer or parylene. This material, in addition to being electrically insulating, is flexible. Each layer 62, 64 and 66 has a thickness of 100 microns or less, often 50 microns or less and, in many preferred versions of the invention, 25 microns or less. Typically each layer 62, 64, or 66 has a thickness of between 10 and 15 microns. Collectively, layers 62, 64 and 66 are shaped so as to provide the illustrated substrate 46 with a center section 68 that has a generally rectangular shape. A head 70 extends forward from the front end, the distal end, of the substrate center section 68. Substrate head 70 is shaped to have two tapered sides (not identified) that, as they extend forward of the center section, taper inwardly toward each other. The head 70 also has a curved front edge, (not identified) that extends between the distal most ends of the sides. Thus, the most distal end of the substrate head 70 has a convex profile.

A tail 74 extends away from the proximal end of the substrate center section 68, the end opposite the distal end. Tail 74 is generally in the shape of truncated triangle. As the sides of the tail 74 extend away from the proximal end of the substrate center section 68, the sides taper inwardly toward each other. In the illustrated version of the invention, the sides of the tail are asymmetric. This shape is only for purposes of illustration and is not intended to be limiting.

Array substrate 46 is further formed to have a number of slots 78 that extend through layers 62, 64, and 66. Each slot 78 is I-shaped. Slots 78 are formed so that the long center sections of the slots are parallel to the longitudinal axis of the substrate, the axis that extends between the opposed distal and proximal ends. The slots 78 are further arranged in pairs such that two slots 78 that are laterally spaced apart from each other are formed in a number of different longitudinally spaced apart portions of the substrate center section 68. In the illustrated version of the invention, the slots 78 are arranged so that each pair of slots is symmetrically positioned relative to the substrate longitudinal axis.

Two slots 80 extend through the substrate head 70. Each slot 80 is generally in the shape of an inverted T wherein the horizontal section of each slot 80 is located slightly forward of and is parallel with the most distal horizontal portion of on the most distally located slots 78.

Figure 5:
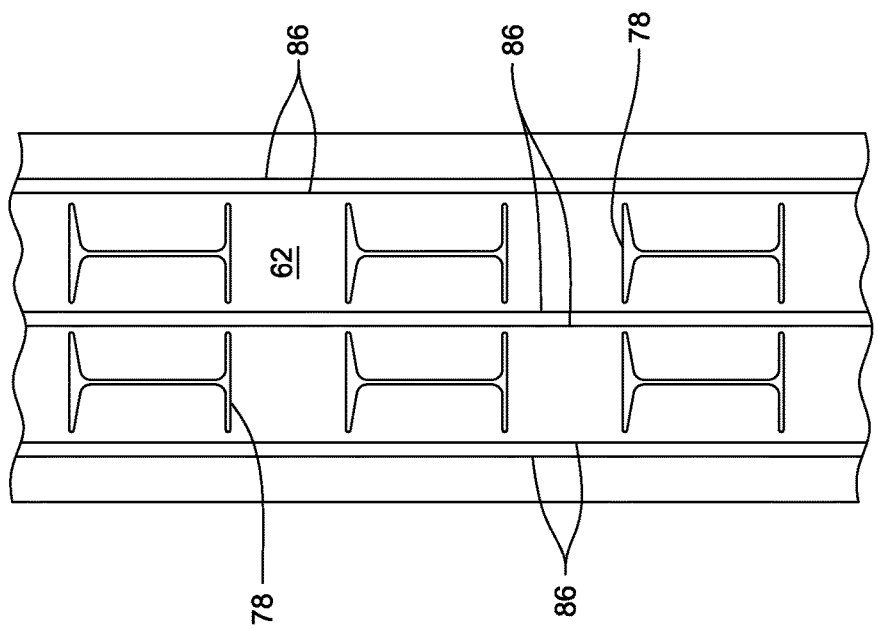
FIG. 5 is a plan view of a section of the upwardly directed surface of the bottom layer of the array substrate.

Conductors that form bus 48 are disposed between the substrate layers 62, 64 and 66. Specifically a set of longitudinally extending conductors 86 are formed on the face of the substrate bottom layer 62, seen in FIG. 5, against which middle layer 64 is disposed. In FIG. 5 each set of conductors 86 is shown to have just two conductors 86. This is for ease of illustration. Typically there are additional conductors 86. Often each set of conductors 86 includes 16 or less conductors and in some preferred versions of the invention, each set of conductor consists of 8 or less conductors. Each conductor 86 is formed from gold has a side-to-side width of 100 microns or less and often 50 microns or less. Each conductor 86 has a thickness of 25 microns or less and more preferably 10 microns or less. Conductors 86 are arranged so that one set of conductors is centered on the longitudinal axis of the substrate. The other two sets of conductors 86 are located between the outer edges of the layer 62 and the portions of the adjacent slots 78 formed in the layers. The center set of conductors 86 extends proximally forward from a location over the tail-defining portion of the substrate layer 62. More particularly, the center conductors 86 terminate in an area over which transfer package 51 is disposed. The outer two sets of conductors 86 extend forward from a location distally forward of the proximal end terminus of the center-located set of conductors 86.

Figure 6:
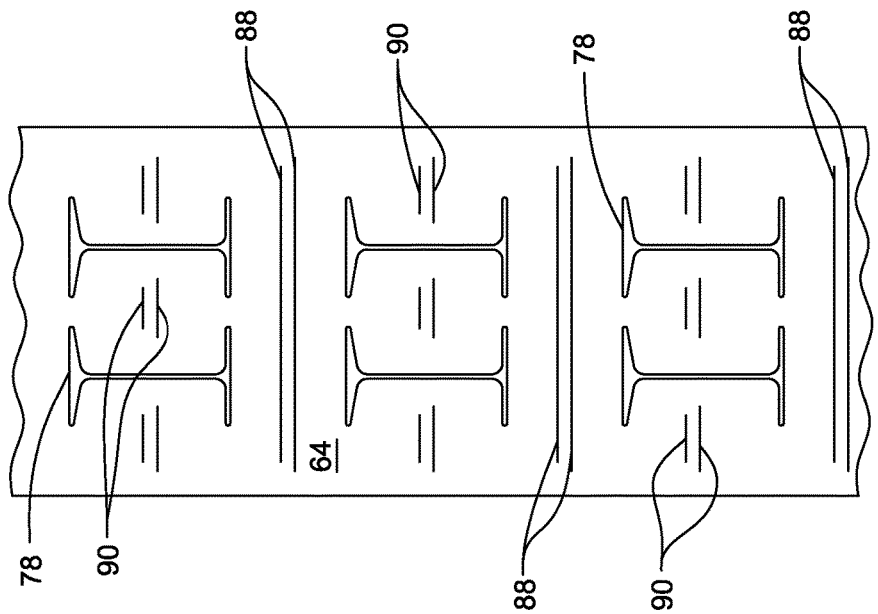
FIG. 6 is a plan view of a section of the upwardly directed surface of the middle layer of the array substrate.

Bus 48 includes a second set of conductors, conductors 88, seen best in FIG. 6. Conductors 88 are disposed on the surface of substrate middle layer 64 that is located between the middle layer 64 and the upper layer 66. Bus conductors 88 are formed from the same material and have the same width and thickness dimensions as bus conductors 86. Bus conductors 88 are disposed over substrate middle layer 64 along axes perpendicular to the longitudinal axis of the substrate 46. Bus conductors 88 are arranged so as to be in plural sets of conductors that are longitudinally spaced apart from each other along the length of the substrate 46. Each set of bus of conductors 88 contains the same number of conductors that are contained in the sets of conductors 86. Sets of bus conductors 88 extend over the portions of substrate middle layer 64 located between the rows of slots 78 formed in the layer. Each bus conductor 88 extends over the underlying three sets of conductors 86; the two outer sets of conductors 86 and the center-located set of conductors 86. The most proximally located set of conductors 88 extends over the portion of the layer 64 immediately proximal to the proximal most row of slots 86.

Also disposed on the same surface of the substrate middle layer 64 on which bus conductors 88 are disposed are branch conductors 90. Each set of branch conductors 90 includes the same number of conductors as there are in the sets of bus conductors 86 and 88. Branch conductors 90 have the same widths and thicknesses of the bus conductors 86 and 88. Branch conductors 90 are disposed on sections of the substrate middle layer 64 in which slots 78 are formed. More particularly, in each of these sections of substrate middle layer 64 there are three parallel, laterally spaced apart sets of branch conductors 90. On each section of the substrate middle layer 64, a first set of branch conductors 90 is located between the slots 78. The remaining two sets of branch conductors 90 are located between each slot 78 and the adjacent side edge of the substrate middle layer. In the illustrated version of the invention, branch conductors 90 are parallel to the coplanar bus conductors 88. In alternative versions of the invention conductors 88 and 90 may not have this relationship and/or conductors 90 may not be linear.

Figure 7:
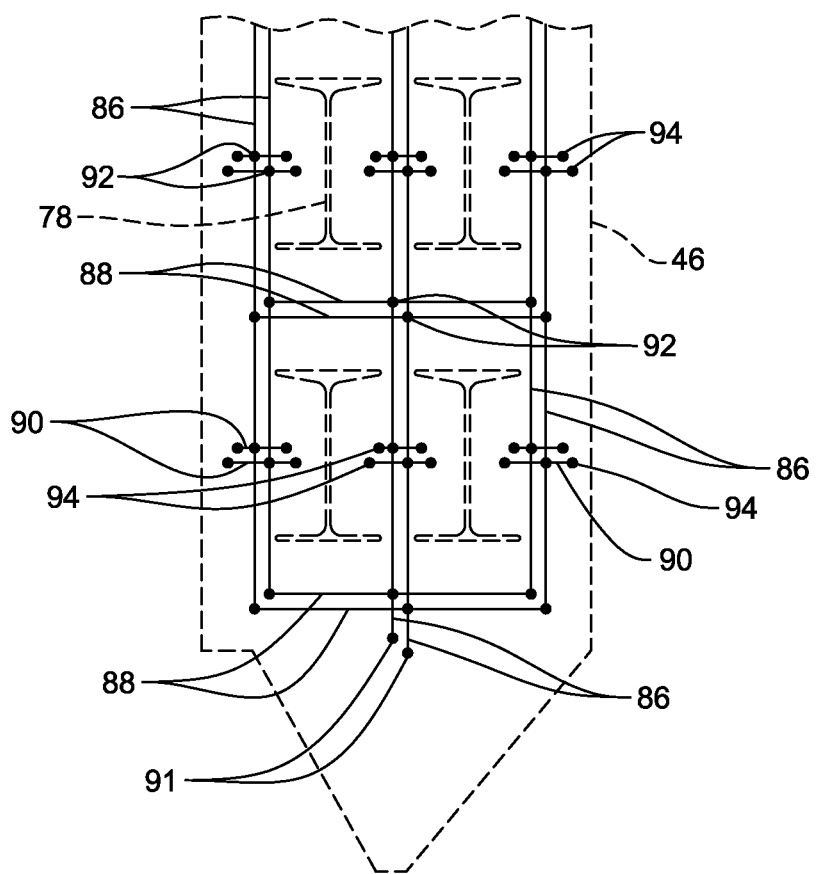
FIG. 7 is a diagrammatic illustrate of the conductors forming the on-substrate bus.

FIG. 7 illustrates the structure of bus 48 and the relationship of branch conductors 90 to the bus. For a point of reference, in FIG. 7, the perimeters of the array substrate 46 and slots 78 are shown in phantom. Conductors 86, 88 and 90 are shown as solid lines. In FIG. 7, the two conductors 86 of the center-located set of conductors 86 are shown having proximal end terminuses that are longitudinally spaced apart from each other. This may be the case when the transfer package 51 is provided with bond pads 237 (FIG. 11) that have a like longitudinal spacing. Vias 91, represented as solid dots in FIG. 7, extend through both the substrate middle and top layers 64 and 66, respectively, connect each of the transfer package bond pads 237 to a specific center-located conductor 86.

Each bus conductor 88 connects one of the center located conductors 86 to the two corresponding outer-located conductors 86, (one conductor 86 on each side of the substrate 46. These connections are made by vias 92 that extend through the substrate middle layer 64, vias 92 represented by solid dots. Each center located conductor 86 is connected to the complementary outer-located conductors 86 by a plurality of longitudinally spaced apart bus conductors 88. This arrangement facilitates equalization of electrical potential along the connected conductors 86. Also, in the event any one bus conductor 88 or associated via 92 fails, the connection to the outer-located conductors 86 is maintained by the remaining conductors 88 and vias 92.

Each branch conductor 90 is connected to a complementary one of the underlying bus conductors 86. This connection is made by one of the vias 92 that extend through substrate middle layer 64. A via 94 extends from each of the each branch conductor 90 through the overlying substrate top layer 66. Each via 94 connects the branch conductor 90 to a bond pad 154 (FIG. 9) integral with the overlying EAP 44.

Frame 50 provides structural support to the rest of the electrode array 40. In most versions of the invention, frame 50 is provided with material that, in addition to providing structural strength to array 40, is flexible, though less flexible than substrate 46 and shell 56. In many versions of the invention, frame 50 is formed out of material that, in addition to being flexible, is super elastic. Here a "super elastic" material is understood to be a material that, in addition to being deformable, after the force holding the material in the deformed shape is removed, returns to its original shape. One such material having the property of being super elastic is a nickel titanium alloy known as Nitinol. In some versions of the invention, frame 50 is formed out a piece of Nitinol having a thickness that is typically 100 microns or less and often in the range of 30 to 70 microns.

Figure 8:
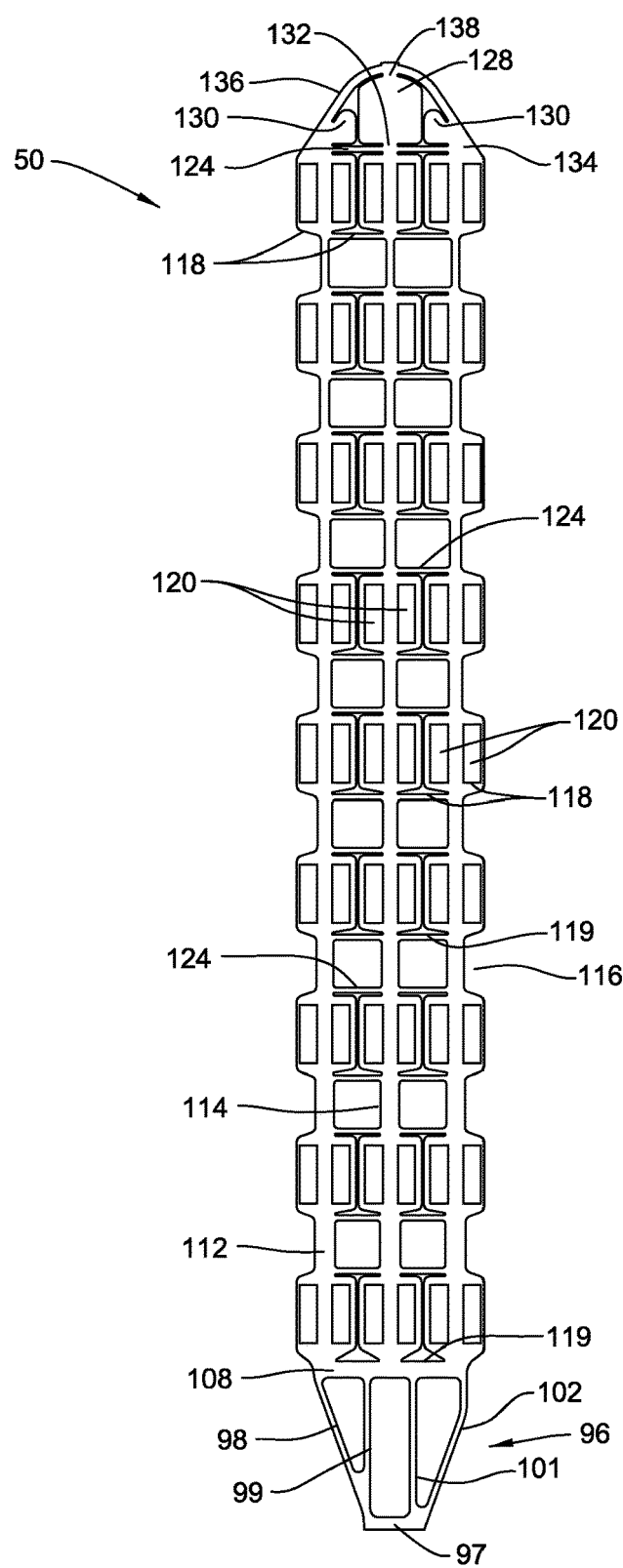
FIG. 8 is a plan view of the array frame.

As seen best in FIG. 8, frame 50 is formed from a single piece of Nitinol and is shaped to have a proximal located tail 96. Frame 50 also has a head 128 that is spaced forward of tail 96. Three parallel spaced apart bridges 112, 114 and 116, extend from the frame tail 96 towards the frame head 128.

Frame tail 96 includes two beams 97 and 108 that extend perpendicular to the longitudinal axis of the array 40. Beam 97, the more proximal of the two beams, is the shorter of the two beams. Beam 108, in addition to being located forward of beam 97, is longer in length than beam 97. Both beams 97 and 108 are centered on the longitudinal axis of the array 40. Four beams 98, 99, 101 and 102 extend between beams 97 and 98. Beams 99 and 101 are perpendicular to beams 97 and extend along axes parallel to the longitudinal axis of frame 50. Beams 98 and 102 taper outwardly from beam 97 so as to extend to the outer ends of beams 108. In the illustrated versions of the invention, beam 98 extends from a proximal terminus that is distally forward of the location from which beam 107 extends. Not identified is the web between beams 98 and 99. Frame tail 96 occupies a surface that is substantially identical to that of substrate tail 74.

Bridges 112, 114 and 116 extend distally forward from beam 108. Bridge 114 is centered along the longitudinal axis of the frame 50. Bridges 112 and 116 are spaced apart symmetrically relative to bridge 114. A number of three-sided tabs 118 extend outwardly from bridges 112, 114 and 116. Frame 50 is shaped so that tabs 118 have major axes that are parallel to the longitudinal axis of the frame. Tabs 118 are arranged in pairs; where a tab 118 extends outwardly from one side of a bridge 112, 114 or 116, a laterally aligned tab 118 extends outwardly from the opposed side of the same bridge. The tabs 118 are further so that where the tabs extend outwardly from one bridge 112, 114 and 116 tabs also extend outwardly from the laterally adjacent sections of the other two bridges. Frame 50 is therefore constructed so that the tabs 50 are arranged in rows wherein, in the illustrated version of the invention, there are six tabs in each row. The rows of tabs 118 are longitudinally spaced apart from each other.

In some versions of the invention, frame is shaped so that the tabs 118 have a length, distance along the axis parallel to the longitudinal axis of the frame 50, of between approximately 0.5 and 4.0 mm. The width of the tabs 118, the distance the tab extends away from the associated bridge 112, 114 or 116, of between approximately 0.5 and 2.0 mm. The frame 50 is formed so that each row of tabs 50 is spaced approximately 0.5 to 4.0 mm away from the row of laterally adjacent tabs. It should be further understood that frame 50 is further shaped so that each tab 118 that extends outwardly from center located bridge 114 is spaced away from the adjacent tab that extends outwardly from the adjacent bridge 112 or 116. This separation is typically a minimum of 100 microns.

Frame 50 is further formed so that each tab 118 is shaped to have a center located rectangular opening 120. The major axes of the tab openings 120 are, centered on the major axes of the tabs 118. Also the outermost tabs 118, the tabs that extend outwardly from the outer side edges of bridges 112 and 116, have tapered front and rear sections, the sections perpendicular to the longitudinal axis of the frame. These sections (not identified) are tapered so that that length of the tab 118 decreases slightly as the tab extends away from the bridge 112 or 116 with which the tab is integral. The outer corners of the tabs (corners not identified) are rounded.

A number of rectangularly shaped beams 124, also part of frame 50, connect bridges 112, 114 and 116 together. The frame 50 is shaped so that where a beam 124 extends between bridge 112 and bridge 114 a laterally adjacent beam 124 extends between bridge 114 and bridge 116. The beams 124 are arranged so that a pair of laterally adjacent beams is located immediately in front of and rearward of all but the most proximal row of tabs 118. A pair of beams 124 are located immediately forward of the most proximal row of tabs 118. In the illustrated version of the invention, there are nine rows of tabs; accordingly there are 18 pairs of laterally adjacent beams. Each beam 124 has a width, the distance parallel to the longitudinal axis of the frame 50, that is typically 2.0 mm or less and often 0.5 mm or less.

In the illustrated version of the invention, frame 50 is further formed so that as the frame extends distally from tail 96, the widths of the bridges 112, 114 and 116 decrease. For example in some versions of the invention, the width of each bridge 112, 114 and 116 immediately forward of the proximal most row of tabs is approximately 0.88 mm. The width of each bridge 112, 114 and 116, between the second and third most proximal rows of tabs is approximately 0.80 mm. The width of each bridge 112, 114 and 116 immediately rearward of the distal most row of tabs 118 is approximately 0.32 mm.

As described above, the tabs 118 that extend outwardly from bridge 114 are spaced away from the adjacent tabs 118 integral with bridges 112 and 116. The tabs 118 are spaced longitudinally away from the adjacent inter bridge beams 124. Thus, between bridges 112 and 1114 and between bridges 114 and 116 there are I-shaped slots 119 around the tabs 118. Frame 50 is further shaped so as to have openings in adjacent tail beam 108 that form slots 119 around the proximal most tabs 118.

The distal end of center bridge 114 is longitudinally aligned with frame head 128. The frame 50 of electrode array 40 is further formed to have two shoulders 130 that are located on opposed sides of head 128. Head 128 is located forward from a small neck 132 that forms the distal end of center-located bridge 114. Thus, neck 132 is located forward of the two distal most tabs 118 that extend outwardly from bridge 114. Each of the two distal most beams 124 extend from neck 132. Head 128 is located forward of the two distal most beams 124. Head 128 has a proximal edge that extends laterally beyond neck 132 on either side of the neck. The head 128 has two parallel side edges. At the most distal end, head 72 has an outwardly curved distally-directed front edge (not identified).

Each shoulder 130 extends forward from a small land 134 located forward of the associated outer bridge 112 or 116. Each land 134 is integral with and extends distally forward from the outer tab 118 integral with the bridge 112 or 114 with which the tab is integral. Lands 134 serve as the terminuses for the beams 124 that extend from neck 132. Each shoulder 130 is spaced forward and away from the adjacent beam 124. Shoulders 130 are also spaced laterally away from the adjacent side edges of the head 128. Specifically, the shoulder 130 on the left side of FIG. 8 is spaced from the adjacent head side edge along a line that is collinear with the line along which the tabs 118 associated with bridge 112 are spaced from the adjacent tabs 118 associated with bridge 114. Similarly, the shoulder 130 on the right side of FIG. 8 is spaced from the adjacent head side edge along a line collinear with the line along which the tabs associated with bridge 114 are spaced from the adjacent tabs 118 associated with bridge 116.

Each shoulder 130 is approximately in the shape of a right angle triangle wherein the 90° corner is located adjacent the bottom of the adjacent side of edge of the head 128. The hypotenuse edge of the shoulder 130 is the outer edge of the shoulder. Each shoulder 130 is, however, further shaped to have a rounded distal end (not identified).

A beam 136 connects the hypotenuse of each shoulder 130 to the top of head 128. Each beam 130 extends from an outer extension of the associated shoulder forward and inwardly. Thus, each beam 136 is spaced forward from the distal end of the associated shoulder 80 and curves inwardly over the adjacent side of the front edge of head 128. The inner end of each beam 136 is connected to a small nose 138 that extends forward from the most forward edge of head 72. Thus, between each shoulder 130 and associated beam 136 there is a small void space (not identified) that generally has the shape of an arrow head. Adjacent each side of nose 138 there is a small curved slot (not identified) between each beam 136 and the adjacent distal end edge of the head 128. This slot is contiguous with the void space between the beam 136 and the adjacent shoulder 130. In FIG. 8, a small tab is seen to extend forward from frame nose 138 (tab not identified). This tab is present for manufacturing reasons and is otherwise not relevant to this invention.

Collectively, substrate 46 and frame 50 are constructed so that when the frame 50 is disposed over the substrate, frame slots 119 are in registration with substrate slots 78. Also, the gaps between the distal most frame beam 124, the frame head 128 and the frame shoulders 130 are in registration over substrate slots 80.

In some versions of the invention, frame 50 may be shaped so as to be non planar. For example the frame may be shaped so as to have a radius of curvature that is perpendicular to the longitudinal axis of the frame. In these versions of the invention, array bridge 114 would thus appear to be above (or below) bridges 112 and 116. Frame 50 would be so curved if it is desirable to provide the array itself with such a curvature. This would facilitate deploying the array 40 against tissue with a similar curvature.

Figure 9:
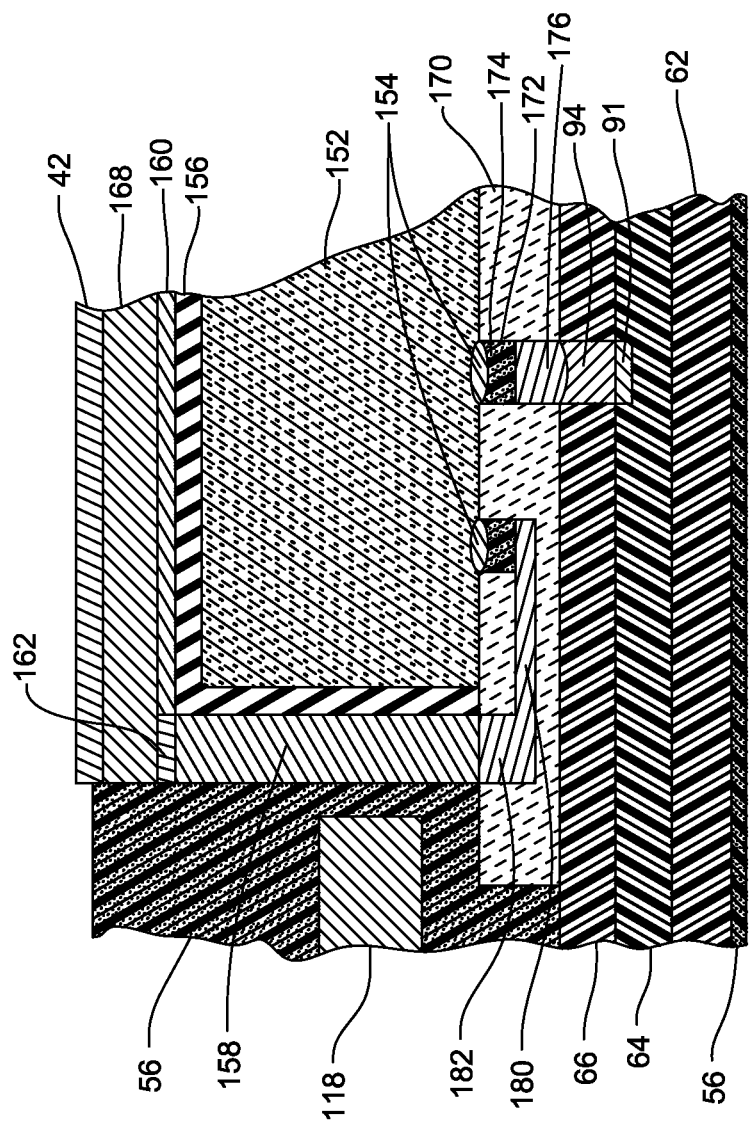
FIG. 9 is a cross sectional view of a portion of an electrode ASIC package (EAP) of this invention as the EAP is embedded in the array.

An EAP 44 of this invention is now described by reference to FIGS. 3 and 9. The EAP 44 includes an application specific integrated circuit (ASIC) 152 that, in response to instructions received over bus 48, selectively sources and/or sinks current to the associated electrode 42. The illustrated ASIC 152 is a six sided polyhedron wherein the surfaces are all rectangular. The bottom surface of the ASIC 152 is provided with a number of gold bond pads 154 (only two shown in FIG. 9). A layer of insulating material 156 such as silicone is disposed over the top and side surfaces of the ASIC 152 so as to form an insulating shell over the ASIC. Insulating material 156 typically has a thickness of 50 microns or less. A frame 158 formed of gold or other conductive material is disposed around the outer surface of the insulating material 156, More particularly, the frame 158 is disposed around the sections of insulating material that are disposed around the four side surfaces of the ASIC 152. This conductive frame 158 has a thickness of at least 5 microns.

A very thin layer of titanium 160 is disposed over the section of insulating layer 156 disposed over the top of the ASIC 152. Titanium layer 160 has a thickness that is typically 5 microns or less. The titanium layer 160 extends above the exposed rectangular face of frame 158 that surrounds the top of the ASIC 152.

A cap 168 formed of gold or other conductive material is disposed over both titanium layer 160 and the adjacent face of frame 158. Cap 168 has a thickness of at least 10 microns. A gold-tin solder layer 162 disposed between the face of the frame 158 and the overlying portion of the cap 168. Solder layer 162 establishes a conductive bond between frame 158 and cap 168. Titanium layer 160 is added to the under construction EAP 44 prior to the application of the solder layer 162. The titanium layer 160 prevents the run off of the solder forming layer 162 over the top of the ASIC 152.

The electrode 42 of the EAP 44 is disposed over the exposed face of the cap 168. In one version of the invention, the electrode 42 comprises a layer of iridium oxide plated over the exposed face of cap 168. The plating forming the electrode 42 has a thickness of at least 1 micron.

As discussed below in more detail, when array 40 of this invention is assembled, the frame-encased ASICs 152 are disposed in frame tab openings 120. Accordingly, the cross sectional area subtended by each ASIC 152 the surrounding conductive frame 158 is less than that of the associated window 120. In some versions of array 40, the components are constructed so that there will be a gap of at least 1 micron between the faces of the array frame 50 that define the tab openings 120 and the adjacent faces of the EAP conductive frame 158.

The EAP 44 also includes a substrate 170 formed from a low temperature co-fired ceramic or other electrically insulating material. Sometimes in this document, substrates 170 are referred to as "package substrates 170" to distinguish them from the array substrate 46. Each package substrate 170 is disposed under the face of the ASIC 152 opposite the face over which the electrode 42 is formed. In terms of relative dimensions, each package substrate 170 has a thickness of that is typically at least 10 microns or more and often 20 microns or more. The substrate 170 is further dimensioned to extend laterally at least 10 microns and often 20 microns or more beyond the outer faces of frame 158. Given the differences in the materials in which the array substrate 46 and the package substrates 170 are formed, it should be appreciated that the package substrates 170 are appreciably more rigid than the array substrate 46.

While not apparent from the Figures, each substrate 170 may be formed from multiple layers of material. In the illustrated version of the invention, each package substrate is formed so as to define closed-ended bores 172 that extend downwardly from surface of the substrate against which the ASIC 152 is disposed. One end of each of these bores 172 is filled with a conductive adhesive 174 such as a conductive polymer adhesive. Below all but one of the adhesive filled bores 172 substrate 170 is formed to have conductive plugs 176. Plugs 176, which may be formed from gold, extend slightly below the face of the substrate 170, for example, approximately 10 microns below the face of the substrate.

A conductive trace 180 is embedded in the package substrate 170. Trace 180 may be formed from gold and have a thickness of at least 1 micron and a width of at least 10 microns. One end of trace 180 is located below and functions as the base of one of the bores 172. The opposed end of the trace 180 terminates at a via 182 that extends through the substrate 170. Via 182 extends to the face of the substrate 170 on which the ASIC 152 is mounted. Via 182 extends to the face of the perimeter section of the substrate, the section of the substrate located outwardly away from the ASIC 152. More particularly, the via 182 is positioned so that when the frame-encased ASIC 152 is disposed over the substrate 170, the base of the ASIC frame 158 is disposed over and in contact with the via 182.

When the EAP 44 is assembled, each of the ASIC bond pads 154 is disposed over one of the substrate bores 172. Each ASIC bond pad 154 is therefore in contact with one of adhesive plugs 174 disposed in the bores 172. One of the ASIC bond pads 154, specifically the bond pad through which signals are sourced to and sunk from the electrode 42, is bonded to the adhesive plug in contact with the substrate trace 180. The adhesive plug 174, the conductive trace 180 and the via 182 integral with the substrate 170 form a conductive path between this ASIC bond pad 154 and the conductive frame 158 that surrounds the ASIC 152. Frame 158, solder layer 162 and cap 168 function as the conductive elements of the EAP 44 over which signals are exchanged between the conductive components of the package substrate 170 and the EAP electrode 42.

Figure 10:
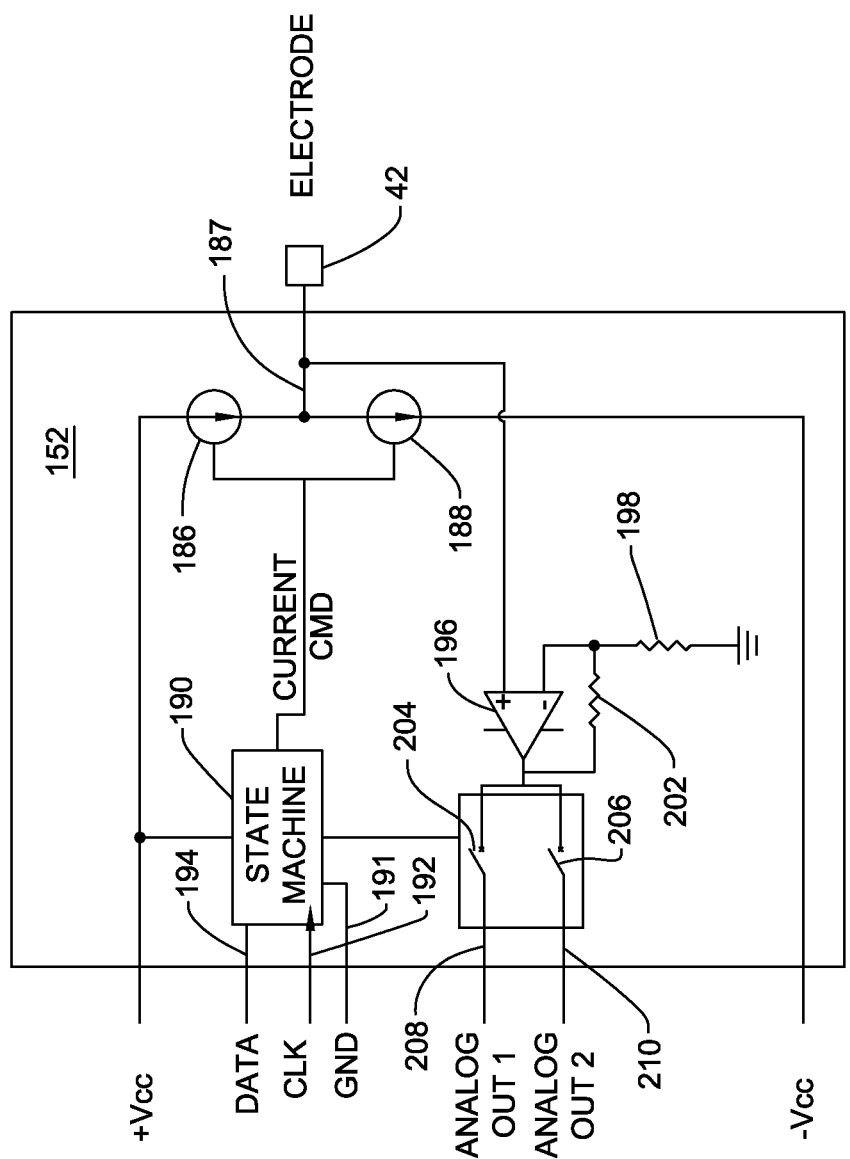
FIG. 10 is a block diagram of the electrical components integral with the electrode ASIC package.

The components internal to a semiconductor die forming an ASIC 152 are now described by reference to FIG. 10. These components include a current source 186 to which a current sink 188 is connected in series. A conductor 187 internal to the ASIC that extends to the electrode 42 is connected to the junction of the current source 186 and current sink 188. Not shown in FIG. 10 are the components outside of the ASIC 152 that establish the conductive path between the conductor 187 and the electrode 42. Power for actuating the current source 186 and current sink 188 come respectively from $^+$Vcc and $^-$Vcc pins (the bond pads 154 to which these signals are supplied.

A state machine 190, also part of ASIC 152, both controls the on/off state of the current source 186 and current sink 188 as well as the level of current these components, respectively, source and sink. Three conductors extend to the state machine 190. A first conductor, conductor 191 serves as the ground conductor. While not illustrated, branches of the conductor 191 extend to the other circuits internal to the ASIC such as the current source 186 and current sink 188. A conductor 192 is the conductor over which clock signals are applied to the state machine 190. Data signals, the actual instructions that regulate the operation of the ASIC and, by extension, the associated electrode 42, are applied to the state machine 190 over the third conductor, conductor 194.

An op amp 196 is connected to conductor 184 to monitor the voltage across the electrode 42. Op amp 196 is operated as a non-inverting amplifier; conductor 187 is connected to the non-inverting pin of the amplifier. A resistor 198 is tied between the inverting input of the amplifier 196 and ground. A resistor 202 is tied between the inverting input and the output. The ASIC 152 has two outputs, conductors 208 and 210 from the output of amplifier 196. Each of the outputs 208 and 210 is connected to a separate one of the conductors integral with bus 48. Two switches 204 and 206 selectively connect, respectively, conductors 208 and 210 to the output pin of amplifier 196. State machine 190 regulates the open/closed state of the switches 204 and 206. The selective setting of the switches 204 and 206 allows the output signal from amplifier to be selectively applied to either one of the two bus conductors. To monitor operation of the array 40, it is often desirable for the implantable device controller to simultaneously receive signals from bus 48 indicating the voltage present at at least two electrodes 42.

Figure 11:
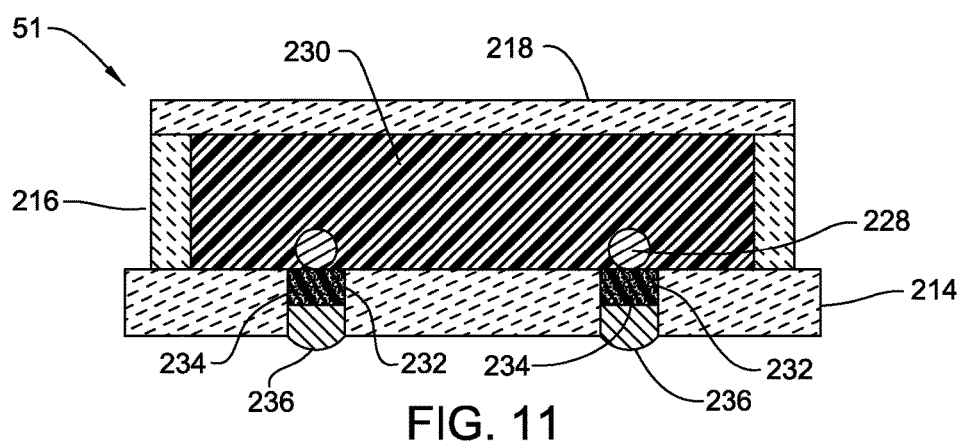
FIG. 11 is a cross sectional view of the transfer package.
Figure 12:
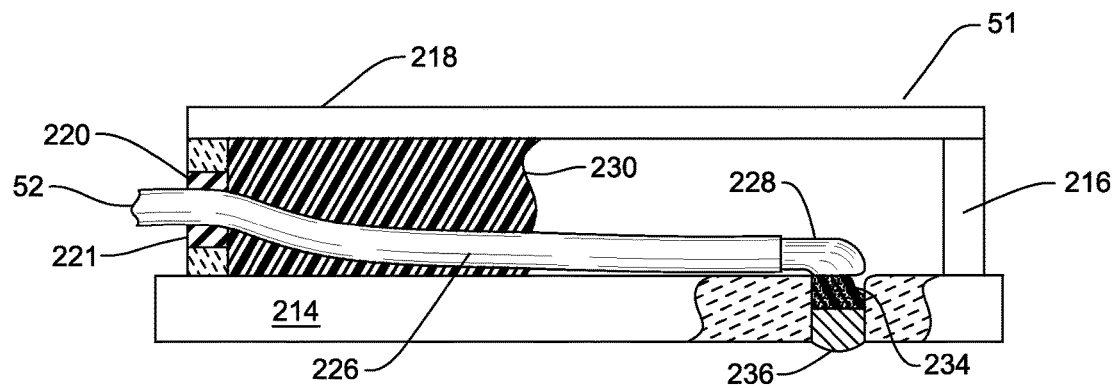
FIG. 12 is an exposed side and partial cross sectional view of the transfer package.

As best seen in FIGS. 11 and 12, transfer package 51 includes a ceramic base 214. A frame 216, also formed from a ceramic, surrounds the outer perimeter of the base 214. In some versions of the invention, the frame 216 may be slightly stepped back from the outer perimeter of the base 214. A cap 218, again formed from ceramic material, is disposed over frame 216.

Package frame 216 is typically formed with one or more openings through which the off-array wires 52 extend into the package 51. In the version of the invention illustrated in FIG. 12, this opening is a through bore 220 in one of the frame-forming panels. In some versions of the invention, this opening is the absence of one of the side panels forming the frame. Alternatively, the opening may consist of a slot that extends from one of the edges of one of the frame-forming panels.

Each wire 52 consists of a conductor (not identified) coated in an insulating material 226. The insulating material is removed from the distal end tips 228 of the wires 52. A potting material 230 encapsulates the wires 52 within the frame 216 between the base 214 and the cap 218. A non-conductive polymer such as silicone may function as the potting material 230. For ease of illustration, in FIG. 12, only a portion of the potting material 230 is illustrated.

Package base 214 is formed to have a number of closed end bores 232. The number of bores 232 corresponds to the number of connections that need to be made from wires 52 to the array bus 48. Each bore 232 extends inwardly from the interior face of the base 214. A plug of conductive adhesive 234 is disposed in each bore 232. A plug of conductive material 236, essential identical to the EAP plugs 176 is located between each adhesive-filed bore 232 of the package base 214. The exposed face of each plug 236, that is the face visible when viewing the exposed surface of the base 214, functions as the bond pad 237 to which one of the substrate vias 91 is bonded. In the illustrated version of the inventions, the plugs 236 are shown as extending a slight distance below the exposed surface of the base 214. This may not always be the case.

In the version of the invention illustrated in FIG. 12, each wire 52 enters the package 51 through one of the openings 220. A seal 221 seated in the opening through 220 between the wire 52 and the surrounding frame panel provides a hermetic barrier between these two components. Seal 221 may be formed from glass or polymer. In some versions of the invention, the cable containing the plurality of wires 52 enters the package through a single opening 220. Inside the package 51, the individual wires are separated from each other.

Inside the package 51, each wire 52 is positioned so that the exposed conductive tip 228 of the wire is bonded to one of the adhesive plugs 234. The potting material 230 is introduced into the frame 216 above the base to fix the wires in the package 51. Cap 218 is then fitted over the frame One part of the process of assembling the components forming electrode array 40 of this invention is the assembly of this invention is the assembly of the substrate 46. Substrate layers 62, 64, and 66 are each formed with the conductors 86, 88, 90 and vias 91, 92 and 94 formed thereon. Layers 62, 64, and 66 are stacked one on top of another. As a consequence of this assembly process, the vias bond to the underlying conductors by an ultrasonic bonding process so as to establish the conductor-to-conductor connections.

The EAPs 44 and transfer package 51 are then bonded to substrate layer 66. A thermal compression process may be used to perform this bonding process. In this process the plugs 176 integral with the EAP package substrates 170 bond to the underlying vias 94. Similarly, the transfer package substrate plugs 176 bond to vias 91. This bonding, sometimes referred to as bump bonding, is what at least temporarily holds the EAPs 44 and the transfer package 51 to the underlying substrate 46. The EAPs 44 the four inner columns of EAPs 44, the four EAPs in each row of EAPs located closest to the longitudinal axis of the array, are disposed on the substrate tabs 78.

Transfer package 51 is disposed over the substrate tail 74 so as to extend over substrate vias 91. Transfer package plugs 236 function as the bond pads for the package. The package 51 is positioned so that each one of the plugs 236 is in registration over the appropriate one of the substrate vias 91. The same process used to hold the EAPs 44 to the substrate 46 are used to hold the transfer package 51 to the substrate. Similarly, the same processes used to bond the EAP plugs 176 to substrate vias 94 is used to bond the transfer package plugs 236 to vias 91.

In some methods of manufacturing array 40 of this invention, a first coat of polymer forming shell 56 is disposed over the partially assembled array. More particularly, in this process step, the initial coating of polymer is applied over the top surface of the substrate of a sufficient depth to extend over the outer exposed perimeter portions of the EAP package substrates 170 and the transfer package base 214. This layer of liquid crystal polymer thus holds the EAPs 44 and transfer package 51 to the array substrate 46. Frame 50 is then disposed over this first polymer layer. Frame 50 is so positioned so that each EAP 44 extends through one of the tab openings 120. Transfer package 51 extends through the opening between frame beams 97, 99, 101 and 108 (opening not identified).

Once frame 50 is positioned relative to the other components of the partially assembled array, a second coating of liquid crystal polymer is applied to the array. This liquid crystal polymer is applied to cover frame 50 as well as to extend to and bond with the outer perimeter of the first coating of liquid crystal polymer. The liquid crystal polymer of this second coating flows into the gaps between the outer perimeters of EAPs 44 and transfer package 51 and the adjacent faces of the frame 51 that define the openings in which the EAPs and transfer package are seated. This second layer of liquid crystal polymer, in addition to completing the formation of shell 56, also serves as the structural component of the array that holds the frame 50 to the rest of the array 40. This second coating of polymer also further fixes the EAPs 44 and transfer package 51 to the rest of the array.

It should be understood that this second coating of liquid crystal polymer is applied in such a manner that shell 56 does not completely cover the EAPs 44. Instead, the relative heights of the shell 56 and EAPs 44 are such that the EAPs extend approximately 5 microns above the outer surface of the shell 56. This means that each electrode 42 of an EAP 44 is exposed. When the array is disposed against tissue through which currents are to be flowed, the EAP electrodes 42 will be in contact with the tissue.

Likewise, the shell-forming polymer does not completely cover the transfer package 51. Accordingly, as illustrated in FIG. 1, the top of the transfer package may extend above shell 56. Owing to its larger height, in comparison to the EAPs 44, the transfer package 51 extends higher above the outer surface of the shell than the EAPs.

In an alternative method of assembling array 40 of this invention, after the EAPs 42 and transfer package 51 are bump bonded to substrate 46, the frame 50 is positioned over and slightly above the substrate. As a consequence of this positioning of the frame 50, the EAPs extend through frame openings 120 by approximately 25 microns, transfer package 51 extends through opening between frame beams 99 and 101 by approximately 150 microns. The EAP 44 and transfer package 51 extend above the frame 50 approximately 25 microns. Polymer forming shell 56 is flowed around over the exposed faces of the substrate 46 and frame 50 as well as in the void space between the substrate and the frame. A fraction of this polymer flows between the EAPs 44 and the adjacent opening defining faces of the frame. Polymer similarly flows between the transfer package 51 and the adjacent sections of the frame. As a consequence of the polymer curing, the EAPs 44 and transfer package 51 are bonded to the substrate 46.

The polymer forming shell 56 is a conformal coating. In both methods of manufacture, this material, when applied, does not bridge the slots 78 and 80 formed in the substrate 48 or the slots 119 formed in the frame 51. Likewise the coating does not bridge between the frame head 128 and shoulders 130. Consequently, upon assembly, electrode array 40, as seen in FIG. 1, has a number of I-shaped slots 235 and inverted T-shaped slots 238. Both slots 235 and 238 extend through shell 56. Slots 235 are aligned with substrate slots 78. Slots 238 are aligned with substrate slots 235. Each row of two slots 235 can therefore be considered to define a row of four tabs 239 in the array 40 that are located inwardly from the outer perimeter of capsule 56. An EAP 44 is embedded in each tab 239. Each row of EAPs 44 thus has four inner EAPs each of which is embedded in one of the array slots and two outer EAPs. Each outer-located EAP 44 is located between the side parameter of array and the outermost tab-embedded EAP.

Once electrode array 40 is assembled, frame 50 functions as a structural lattice that supports the other components of the array. Frame 50 thus holds the rest of the array in a semi-rigid shape. This substantially eliminates the possibility that, post-implantation, the array will undergo uncontrolled flexing or folding. The essential elimination of this movement of the array results in a like elimination that, as a result of such movement, the electrodes 42 will so shift position that they will no longer be located where they can flow current through the tissue through which such current flow will have the desired therapeutic effect.

If the frame 50 is curved, it should be appreciated that the array 40 will have a like shaped curvature.

If the frame is made from supereleastic material, the frame also allows the array to be folded or rolled so that it can be placed in a relatively small deployment instrument. Such an assembly is disclosed in, the Applicants' Assignee's above-mentioned PCT Pub No. WO 2009/111142, FOLDABLE, IMPLANTABLE ELECTRODE ARRAY ASSEMBLY AND TOOL FOR IMPLANTING SAME, the contents of which are incorporated herein by reference. Specifically, the array of this version of the invention is designed to be folded around three axes, the longitudinal axes of frame bridges 112, 114 and 116. When the array 40 is so folded, it should be appreciated that frame beams 108 and 124 are curved, (curve in or out of the plane of FIG. 8). The sections of the substrate 46 between frame bridges 112, 114 and 1124 and below will likewise curve with the bending of the beams 108 and 124. However the array tabs 239 are separate from the surrounding components of the array, in particular, the under curvature beams 124. These tabs 239 which include substrate tabs 79 and frame tabs 118 are not therefore bent/folded to the extent the surrounding portions of the array are bent/folded. Since the tabs are subjected to minimal if any flexure during this array folding process, the EAPs 44 seated on the substrate tabs 79 and in the frame tabs 118, are likewise not subjected to such deformation. The essential elimination of this curving, bending of the EAPs 44 likewise substantially reduces the likelihood that the EAPs could be break apart by such curving. The likelihood that such curving could cause the EAPs to separate from the other components of the array 40, in particular, from the substrate vias 94 is therefore substantially eliminated.

It should be appreciated that when the array 40 is in the folded state, one column of EAPs 44 may be folded/bent/rolled/under a second column of EAPs 44. This means that, when viewed in cross section one would see: a portion of the array substrate 46; the package substrate 170 of a first EAP; the integrated circuit 56 of the first EAP; the electrode 42 of the first EAP 44; electrode 42 of a second EAP; the integrated circuit of the second EAP; the package substrate 170 of the second EAP and a second portion of the array substrate 46.

Once the array 40 is folded or curved, the array can be placed in a delivery device such as a delivery cannula. Given that the array is folded or curved, the array can be disposed in a cannula that has a lumen with a diameter that is less than the width of the array when the array is in the unfolded/unrolled state. In other words the array of this invention, upon being folded/rolled can be placed in a relatively narrow delivery device that allows the array to be inserted percutaneously over the target tissue, the tissue through which the current is to be deployed.

Then, once the array is freed from the constraints of the deployment instrument, the superelastic properties of the frame 50 causes the frame and, by extension, the whole of the array 40 to unfold into the shape in which they should be so as to be properly deployed against the tissue through which the current is to be flowed. If the array 40 has a curved shaped, the curvature of the array increases the likelihood that when the array is deployed, each of the electrodes 42 will be disposed against the similarly curved tissue.

Array 40 of this invention also includes electrodes 42 that are rigidly integral with the components that source/sink current to the electrodes and that measure the voltages developed as a consequence of the current flow through the tissue. This array of this invention therefore does not require the presence of flexible miniaturized connections between the electrodes and the components that source/sink current to/from the electrodes. The essential elimination of these conductors results in a like substantial elimination in the difficulties associated both with their fabrication and fragility.

Moreover, it should he appreciated that the initial conductive path to/from any ASIC bond pad 154 is through the conductive adhesive plugs 174 internal to the associated package substrate 170. The next segment of the conductive path is either the conductive plug 176 or conductive trace 180. The adhesive plugs 174, the conductive plugs 176 and the conductive traces 180 are all rigid within the package substrate 170. The ASIC 152 itself is firmly bonded to the package substrate 170. Collectively, these relationships mean that, while the array substrate 46 may allows for flexibility between the individual EAPs 44, the package substrates 170 and components integral with these substrates ensure that the electrically connections immediately to/from each ASIC 152 are relatively rigid. This rigidity of these connections reduces the likelihood that, when the array 40 is folded, rolled, bent or flexed, the deformations of the array substrate 46 will stress these connections to the point at which the connections may break.

Also, each EAP 44 of this invention can be tested prior to its assembly on an array 40. This reduces the likelihood that an assembled array of this invention will contain a faulty EAP 44.

Still another feature of this invention is that the material forming shell 56 does more than form an outer cover around the other components of the array 40. The shell-forming material is applied in such a manner that it adheres to many if not all of the exposed surfaces of the interior components of the array. The shell thus functions as a matrix which fixes the other components of the array in their assembled positions. This reduces the likelihood that these components could undergo malfunction-causing delamination.

Also, the geometry of the EAPs 44 of this invention is not dependent on the geometry of the other components of the array. Thus, if for a particular application, it is desirable to provide electrodes that have circular, oval or non-rectangular shapes, the EAPs can be designed to be so shaped. Then, the frame that provides structural rigidity to the rest of the array can be shaped to accommodate both the shape and size of the EAPs 44.

II. Second Embodiment

Figure 13:
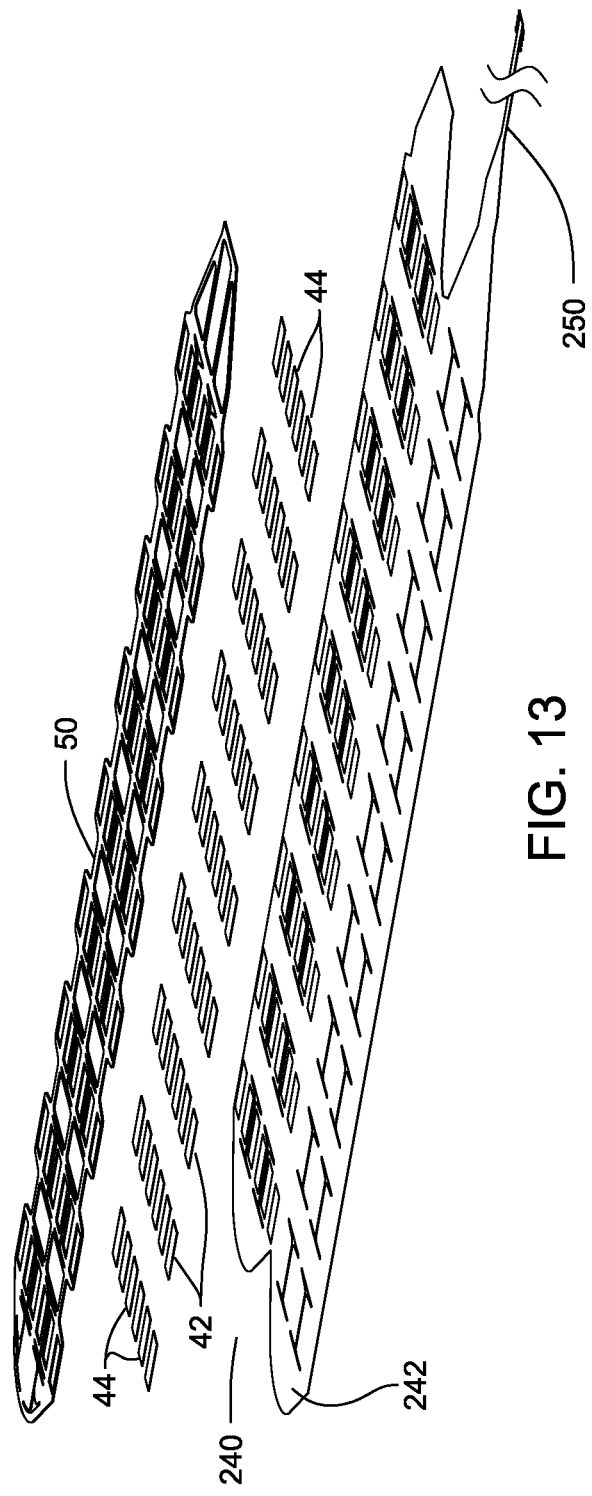
FIG. 13 is an exploded view of an alternative electrode array of this invention.
Figure 14:
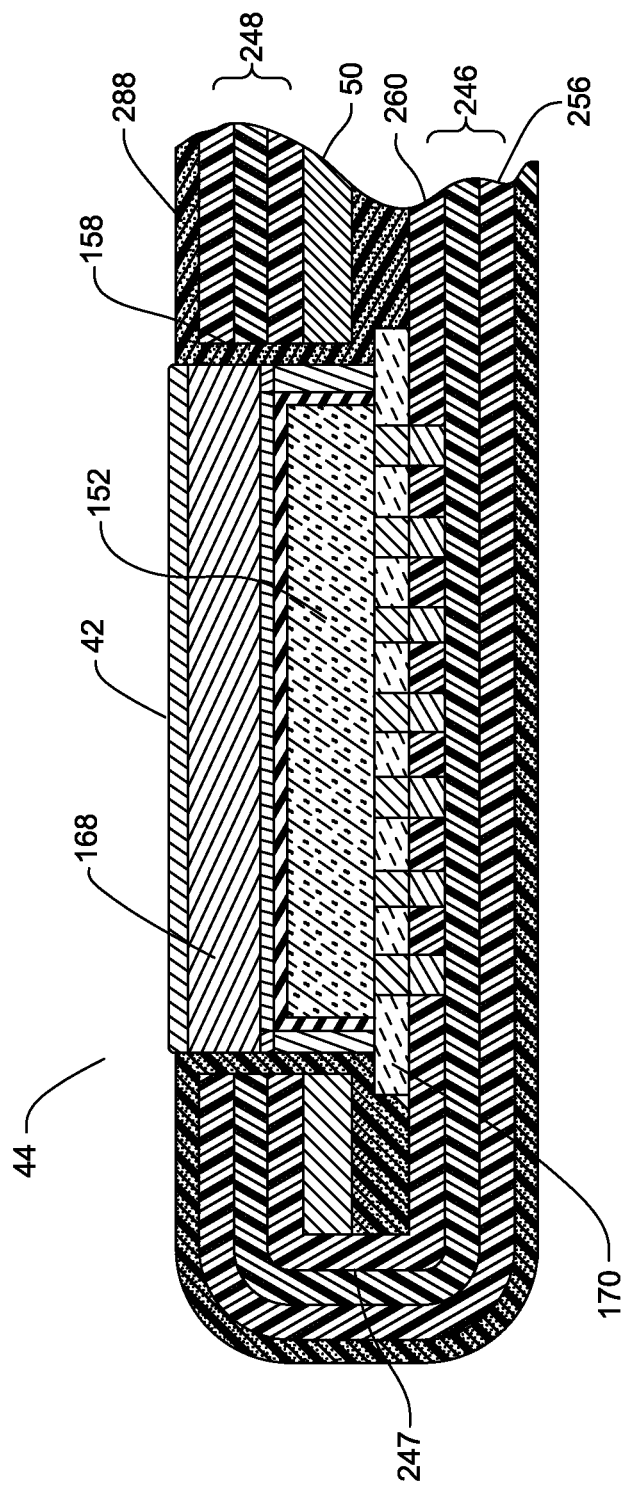
FIG. 14 is a cross sectional view of a portion of the alternative electrode array of FIG. 13.

FIGS. 13 and 14 illustrate an alternative electrode array 240 of this invention. Array 240 includes the EAPs 44 and frame of array 40. Electrode array 240 also includes a flexible sheet 242, seen in FIG. 13, that, upon assembly of the array, as seen in FIG. 14 has a section that becomes a substrate 246 and a section that becomes a superstrate 248. Formed integrally with and extending proximally from sheet 242 is a flexible strip 250. Strip 250 carries the conductors 52 of FIG. 1 that connect the array bus to the implantable device controller.

Figure 15:
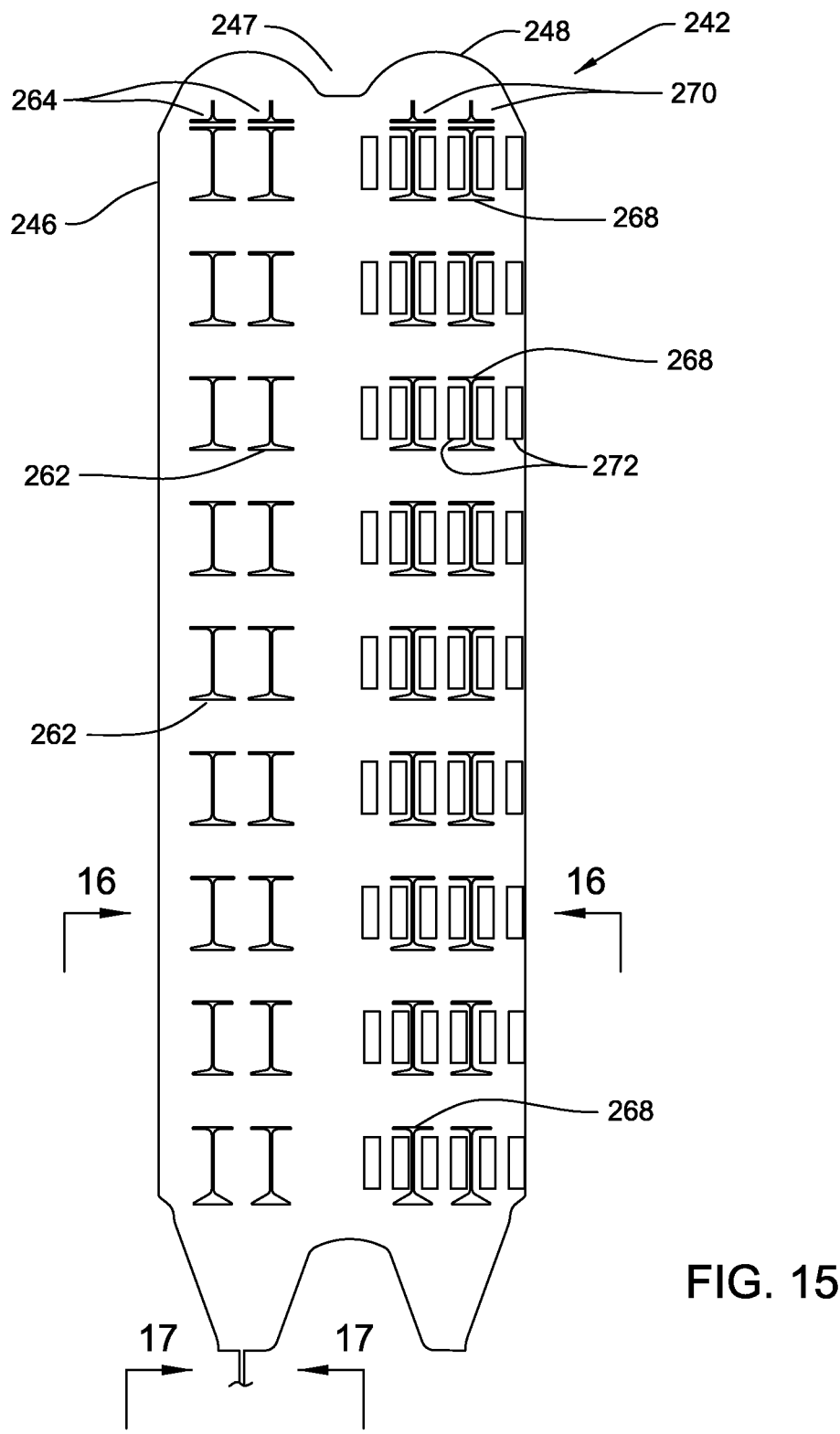
FIG. 15 is a plan view of the unfolded flexible sheet of the electrode array of FIG. 13 that forms the substrate, the hinge and superstrate.
Figure 16:
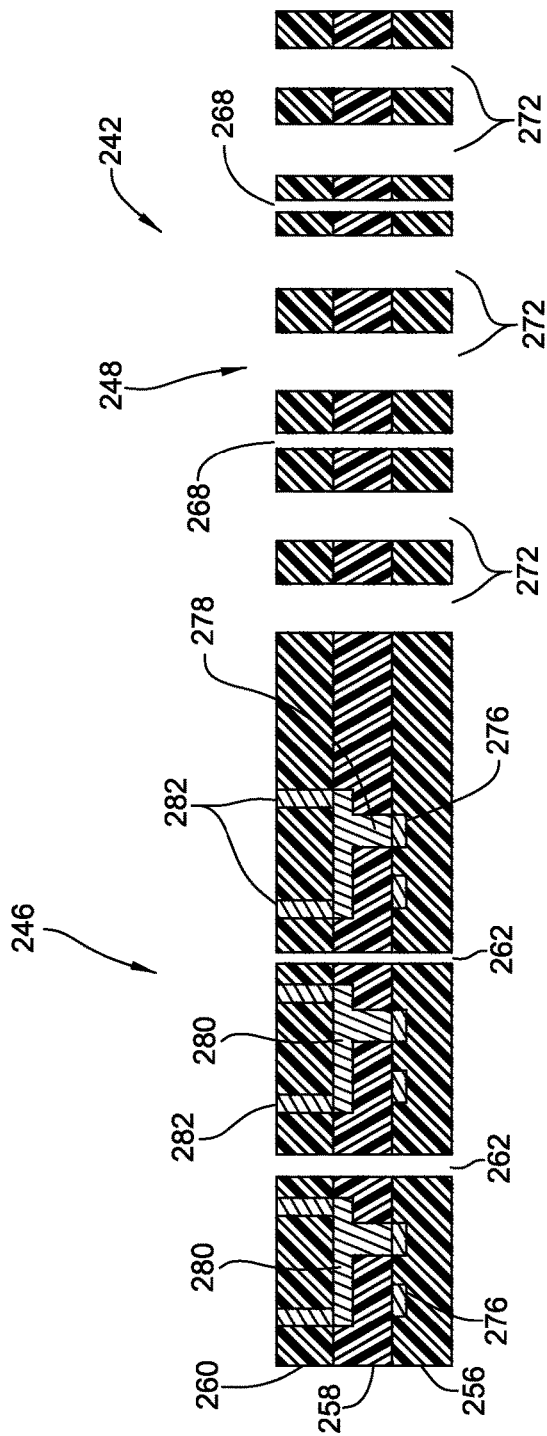
FIG. 16 is a cross sectional view of the sheet of FIG. 15 taken along line 16-16.

Flexible sheet 242, now described by reference to FIGS. 15 and 16, is formed from three layers 256, 258 and 260 of material. Layers 256, 258 and 260, respectively the bottom, middle and upper layers of sheet 242 are formed from the same material and have the same thickness as layers 62, 64 and 66 of substrate 46. Sheet 242 is formed so as to, in the unfolded state, define the substrate 246 and superstrate 248. Between the substrate 246 and superstrate 248, sheet 242 is formed to have a hinge 247. When sheet 242 is in the unfolded state, hinge 247 is coplanar with substrate 246 and superstrate 248.

Layers 256, 258 and 260 are formed to define in the substrate 246 multiple, longitudinally spaced apart rows of slots 262. Slots 262 are analogous to slots 78 of substrate 48. Layers 256, 258 and 260 are also formed so have in the proximal end two slots 264 that are located above the slots 262. Slots 264 are analogous to slots 80 of substrate 48. Layers 256, 258 and 260 are further formed to define in the superstrate section 248 of the sheet 242 multiple rows of I-shaped slots 268. Each row of slots 268 is aligned with a row of slots 262. The number of slots 268 in each row of slots 268 is identical to the number of slots 262 in each row of slots 262. Sheet superstate section 248 is further formed to have plural slots 270 that are laterally aligned with and have the same shape as substrate section slots 264. Flexible sheet 242 is further formed so that when the sheet is curved to bring superstrate 248 in registration over the substrate 246, each slot 268 is in registration over a corresponding slot 262. As a result of this folding of the sheet 242, each slot 270 is likewise in registration over a separate one of the slots 264.

Sheet layers 256, 258 and 260 are further formed so that the section of sheet 242 that forms superstrate 248 has a number of rectangular windows 272. Windows 272 are arranged in plural, laterally spaced apart rows. The number of rows of windows 272 corresponds to the number of rows of EAPs 44. The number of windows 272 in each row corresponds to the number of EAPs 44 in a row of EAPs. In the illustrated version of the invention, there are two columns of slots 268. Flexible sheet 242 is further formed so that between the two slots 268 in a row of slots there are two windows 272. There are also two windows 272 located to the side of each slot 268 opposite the side located proximal to the companion slot 268.

Conductive traces and vias are formed on sheet layers 256 and 258 to perform functions similar to those performed by conductors 86, 88 and 90 of substrate 46. These traces are formed on the section of the flexible sheet that functions as substrate 246. In FIG. 16, six conductive traces 276 are shown formed on sheet bottom layer 256. Traces 276 are coming in and out of the plane of FIG. 16. In the FIG. 16 traces 276 appear embedded in the top of substrate layer 256 and the below discussed traces 280 appear embedded in substrate layer 258. This is for ease of illustration. Conductive traces 276 are analogues to bus conductors 86 of the first embodiment of the invention. Thus traces 276 are the bus conductors that extend longitudinally through array 240.

Conductive traces 280 are shown formed on sections of sheet middle layer 258. Conductive traces 280 are analogues to branch conductors 90 of the first embodiment of the invention. Not illustrated in FIG. 16 are the conductive traces formed on sheet middle layer 256 that are analogues to bus conductors 88. These traces are essentially identical in structure to traces 280 expect that they extend from over the slot free portions of the substrate-forming section of the sheet.

Vias 278 and 282 extend through substrate-forming section of the sheet 242. Vias 278 extend through sheet middle layer 258 to connect conductive traces 276 to traces 280. Other vias 278, (not illustrated,) connect the traces 276 to the traces on layer 258 analogues to the bus conductors 88. Vias 278 are thus analogues to vias 92. Vias 282 extend from ends of conductive traces 280 through substrate upper layer 282. Vias 282 are the conductive paths between the EAP bond pads to traces 280. Vias 282 are thus analogues to vias 94.

Figure 17:
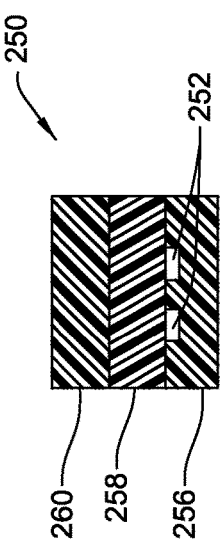
FIG. 17 is a cross sectional view of the sheet of FIG. 16 taken along line 17-17.

In the illustrated version of the invention, proximally extending sections of the bottom, middle and upper layers 258, 260, 262, form strip 250. As seen in FIG. 17, gold traces are formed on strip-forming section of lower layer 258 so as to form conductors 252. Conductors 252 are integral with the gold traces that form the center located conductive traces 276 on the substrate-forming section of the lower layer 258. In some versions of the invention, at the end of the strip 250 spaced furthest from sheet 242, vias (not illustrated) may extend through the strip-forming sections of the middle and upper layers 260 and 262, respectively. These vias serve as the conductive paths between the contacts integral with the implantable device controller and strip conductors 252. Alternatively, in some versions of the invention, middle layer 260 and upper layer 262 are simply not present at the free end of the strip. Owing to the absence of these layers of strip-forming material, the ends of the strip conductors 252 are therefore exposed. The exposed ends of these conductors 252 can then be bonded or otherwise electrically connected to contacts integral with the implantable device controller.

Assembly of electrode array 240 of this invention may begin with fabrication and testing of the EAPs 44 and flexible sheet 242. The EAPs 44 are disposed over the substrate 246 portion of the unfolded sheet 242 and bump bonded to vias 282. Liquid crystal polymer or parylene is applied over the ends of the EAP substrates 170 that project beyond the EAP frames 158. This coating at least temporarily holds the EAPs 44 to the sheet 242. Semi-rigid frame 50 is then fitted around the EAPs 44.

Once frame 50 is in position, sheet hinge section 247 is folded so that the sheet superstrate section 248 is disposed over the substrate section 246. As a consequence of this folding of sheet 242, the EAPs 44 seat in the sheet windows 272; slots 268 go into registration with slots 262; and slots 270 are placed in registration with slots 264. Also as a consequence of this folding process the surface of the superstrate 248 that faces the substrate 246 is pressed against the frame 50. This component-to-component contact serves to temporarily hold the frame to the rest of the partially assembled array 240.

Once sheet 242 is folded so as to temporarily hold the frame 50 in position, a second coating of liquid crystal polymer or parylene is applied to the partially assembled array. The material of this coating is flowed into the gaps between each EAP 44 and the adjacent faces of the frame 50 and superstrate 248. The coating is also flowed over the exposed surfaces of the hinge 247 and superstrate 248. Coating is also applied over the side of the partially-assembled array 240 where the free ends of the substrate 246 and superstrate 248 are present. The layers of coating, when cured, collectively form the flexible shell 288 of the array 240.

Coating may also be applied over flexible strip 250. This coating may or may not be applied to the strip at the time the coating is applied to complete the process of assembling the array 240.

In alternatively constructions of the invention, a coating that, when cured, is flexible, may not be applied to strip 250. Instead a tube formed from biocompatible electrically insulating material such as a liquid crystal polymer may be fitted over strip 250.

An advantage of array 240 of this invention is that flexible sheet 244 performs plural functions. The sheet serves as both a substrate and superstrate for the array. In these capacities, the sheet provides the array with mechanical strength. During assembly of the array the substrate portion of the sheet serves to temporarily hold the frame in position until the coating can be applied to permanently affix the frame in place.

Further, the structural component that carries the conductors 252 that connect the array 240 to the implantable device controller, flexible strip 250, is integral with the sheet. This means that the conductors that are connected to the IDC and at least some of the on-array bus conductors can be formed as a single conductive trace. This eliminates the need to provide the array 240 of this invention with a transfer package.

III. Alternative Embodiments

It should be recognized that the foregoing is directed to specific versions of this invention and that other versions of this invention may have features different from what has been described.

For example, there is no requirement that each of the disclosed features be in each version of the invention. Thus, there may be some versions of the invention in which it is desirable that the array be very flexible. This would allow the array to conform to tissue with irregularly shaped features. In these versions of the invention it may therefore not be necessary to provide the array with a frame that provides structural rigidity.

Likewise, there is no requirement that, in order to provide a flexible strip with the conductors that extend to the off-array IDC, the flexible sheet forming the substrate and strip also be formed to define an array superstrate. Similarly, a flexible sheet that defines the array substrate and superstrate does not always also have to include the conductor-carrying flexible strips.

The components internal to each EAP 44 should likewise be understood as exemplarily and not limiting. In some versions of the invention; some EAPs may have components that allow the integral electrodes to source and/or sink current while other EAPs are used for measuring circuit potential and tissue impedance.

The arrangement of EAPs 44 on an array is not limited to the row by column pattern in the illustrated embodiments of the invention. Similarly the array itself may not have the elongated shape of the described embodiments. In some versions of the invention the array may have a profile that is square, triangular, or even rounded.

Likewise, some arrays of this invention may not be designed for percutaneous implantation. The arrays of these versions of the invention may not have the geometric features that facilitate the folding or rolling of the arrays. These versions of the invention, for example, may not be provided with tab-defining slots around the EAPs.

Furthermore, while it is contemplated that in many versions of the invention each electrode 42 will be part of EAP 44, this may not always be the case. In some versions of the invention, one, more or even all of the electrodes may simply be stand alone components. Conductors extend from the current sources, current sinks and/or current sinks and/or voltage/current monitoring electrodes to these electrodes. This version of the array may be provided if the size of the electrodes is such that any associated packaging would be too small to accommodate the complementary circuit components.

In versions of the invention wherein the electrodes may not be directly formed on the ASIC package, the package substrates 170 may still be used to provide both rigid support for the individual ASICs 152 and serve as the support for the components that provide the relatively rigid electrical connections to/from the ASICs. Vias similar to the vias of the incorporated by reference U.S. patent application Ser. No. 12/535,717 extend through the substrate and any overlapping shell. These vias function as the conductors that extend from the package substrates 170 to the electrodes.

Likewise, there is no requirement that in all versions of this invention, each EAP have only a single electrode. In some versions of this invention, the exposed surface of one or more EAPs may be provided with two or more spaced apart electrodes. In some embodiments of this version of the invention, internal to the EAP is a switch. This switch can be set to selectively connect one or more and less than all of the on-package electrodes to the active current source and/or current sink in the package. Alternatively, in some embodiments of this version of the invention one or more of the EAPs 44, in addition to having plural electrodes 42, has plural current sources, current sinks or amplifiers. Then depending on the instructions received by the EAP, the plural electrodes on the EAP can be simultaneously, sourcing different currents or sinking different currents. Alternatively, one electrode could be sourcing current while an adjacent electrode on the same EAP 44 could be sinking current. Still in another operating configuration of this invention, one electrode on the EAP may be sourcing or sinking current while the second electrode is employed to monitor the voltage across the adjacent tissue.

Furthermore, in the described version of the invention the whole of the exposed surface of the conductive material forming each electrode 42 functions as the electrode. This may not always be the case. In some versions of the invention, electrically insulating material may cover one or more portions of the electrode-forming conductive layer. This conductive layer, instead of being a single electrode thus serves as the component that, in combination with the insulating material forms a plurality of spaced apart electrodes. These spaced apart electrodes, given that they are part of common conductive layer, have a common potential.

Likewise, the electrode ASIC packages of this invention may have physical constructions different from what has been described. Thus, in one alternative electrode ASIC package of this invention, the connection from ASIC semiconductor die to the electrode is through a bond pad on surface of the die closest to the electrode. In this version of the invention, the die is enclosed in a package shell formed from ceramic or other electrically insulating material. Vias on the shell section that abut the package substrate connect the conductors to the complementary bond pads on the die. The electrode is typically formed on the shell section opposite the section disposed against the package substrate. A via in the shell section located between the die and the electrode establishes the electrical connection between the components internal to the semiconductor die and the electrode. An advantage of this version of the invention is that it eliminates the need to provide a conductive frame around the outside of the die to function as the conductive link between the die components and the electrode.

Similarly, given the nature of the components connected to a particular electrode or set of electrodes, it may be necessary to mount plural integrated circuits in a single package assembly. The underlying substrate may then include conductors that provide the electrical connections between the individual integrated circuits.

In some embodiments of the above described version of the invention, there may not even be a need to provide an insulating frame around the EAP die. In these versions of the invention, there would still typically be a layer of insulating material between the die and the overlying conductive material forming the electrode.

Other variations in the construction of the electrode array of this invention are possible. For example, the layers of material forming the substrate on which the conductors are formed may serve an additional function than conductor support components. This material may be formed from semi-rigid material such as silicone. Thus, the substrate in addition to serving as the support for the conductors services as the semi-rigid frame that provides the array with at least a degree of structural definition.

Also, in some versions of the invention, the material forming the substrate can serve as a section of the shell of the array. For example, in these versions of the invention, when the rest of the material forming the shell is applied to the array under assembly, this material bonds to the sides of the material forming the substrate. The substrate thus becomes the section of the shell disposed under the EAPs 44 and any underlying support frame.

Further, in versions of the invention with the frame, there is no requirement that the frame be a single-piece structure. In some versions of the invention, the frame may consist of a plurality of separate structural members that provide the array with more rigidity than is provided by the substrate and/or shell. For example, if the array is intended to be wrapped around a small diameter nerve bundle, the frame may consist of a plurality of elongated individual ribs that extend longitudinally through the array. These ribs may not be connected to each other. Accordingly, the ribs would provide the array with structural rigidity that reduces flexing of the array along axes perpendicular to the ribs while allows the array to be wrapped tightly around an axis parallel to the ribs.

Likewise there may be variations in the method of array manufacture of this invention. For example, the method of folding over a flexible sheet 242 so that one portion of the sheet functions as the array substrate and a second portion of the sheet functions as the array superstrate may be practiced with integrated circuits and electrodes other than the integrated EAP package of this invention. In these alternative versions of the invention, after the integrated circuits are disposed on the substrate-forming section of the flexible sheet and the sheet is folded over, electrodes may be formed on or attached to the superstrate forming portion of the flexible sheet. In alternative versions of this method of manufacture and resultant array, the frame may be omitted.

Accordingly, it is an object of the appended claims to cover all such variations and modifications that come within the true spirit and scope of this invention.

What is claimed is:

1. An electrode array for application against living tissue, said electrode array including:
 a plurality of electrode ASIC packages (EAPs) arranged in an array, each of said plurality of EAPs including:
  an integrated circuit, said integrated circuit shaped to have opposed bottom and top surfaces and having components configured to at least one of: source current through an electrode; sink current from an electrode; or measure a potential at an electrode; and with said integrated circuit including at least one bond pad disposed on the bottom surface for establishing a conductive path to said components of said integrated circuit;
  a package substrate that extends over the bottom surface of integrated circuit, said package substrate having at least one conductive member disposed therein that establishes an electrical connection to said at least one bond pad of said integrated circuit
  a package shell formed from electrically insulating material, said package shell being disposed over said integrated circuit including the top surface of said integrated circuit; and
  at least one electrode disposed over a section of said package shell that is disposed over the top surface of said integrated circuit so as to be rigidly integral with said integrated circuit, said at least one electrode formed from material that can be placed in contact with living tissue and through which current can be sourced to or sunk from the living tissue wherein, said at least one electrode is electrically connected to said components of said integrated circuit;
 an array substrate formed from biocompatible, electrically insulating material, said array substrate having a first outer surface and wherein said package substrates of said plurality of EAPs are mounted to the first outer surface of said array substrate and said array substrate is further formed from material that is more flexible than said package substrates; and
 at least one electrically conductive array conductor mounted to said array substrate over which signals are at least one of transmitted to or received from said components of said integrated circuits, said at least one array conductor being connected to said conductive members of said package substrates so that a conductive path is established through said at least one array conductor, said conductive members of said package substrates and said bond pads of said integrated circuits to the components of said integrated circuits.

2. The electrode array of claim 1, wherein at least one of said EAPs is further formed so that:
said integrated circuit of said EAP further includes at least one side surface that extends between the bottom and top surfaces of said integrated circuit; and
said package shell extends over the at least one side surface of said integrated circuit; and
an electrode conductor extends between said integrated circuit and said electrode of said EAP so as to provide an electrical connection between said components of said integrated circuit and said electrode and said electrode conductor extends over said package shell so as to be disposed over a portion of said package shell that extends over the at least one side surface of said integrated circuit.

3. The electrode array of claim 1, wherein at least one of said EAPs is further formed so that:
said package shell has at least one side surface that extends between the top and bottom surfaces of said integrated circuit;
said package substrate of said EAP is shaped to have a perimeter section that is located laterally outwardly from the side surface of said package shell;
said at least one electrode of said EAP is disposed over said package shell so as to be located over the top surface of said integrated circuit; and
said package substrate is further formed to contain a substrate conductor that extends from the bond pad of said integrated circuit of said EAP through said package substrate from the bottom surface of said integrated circuit to the perimeter section of said package substrate; and
an electrode conductor extends from an end of said substrate conductor located in the perimeter section of said package substrate to said electrode of said EAP to provide an electrical connection between said components of said integrated circuit and said electrode.

4. The electrode array of claim 1, further including an array shell formed from flexible material disposed over said array substrate and around said package substrates of said plurality of EAPs.

5. The electrode array of claim 1, wherein:
said array substrate is formed to have a second outer surface opposite the first outer surface; and
an array shell formed from flexible material is disposed over the first and second outer surfaces of said array substrate and around said package substrates of said plurality of EAPs.

6. The electrode array of claim 1, wherein:
an array shell formed from flexible material is disposed over the first surface of said array substrate and around said package substrates of said plurality of EAPs; and
a frame is embedded in said array shell, said frame being more rigid than said array shell.

7. The electrode array of claim 1, wherein:
an array shell formed from flexible material is disposed over the first surface of said array substrate and around said package substrates of said plurality of EAPs; and
a frame is embedded in said array shell, said frame being more rigid than said array shell and being formed with windows and wherein said frame is embedded in said array shell so that said plurality of EAPs are seated in the windows of said frame.

8. The electrode array of claim 1, wherein said array substrate is a laminate formed from plural layers of material.

9. The electrode array of claim 1, wherein:
at least one of said EAPs has a package shell with a side surface that extends between the top and bottom surfaces of said integrated circuit of said at least one EAP and said package substrate of said at least one EAP has a perimeter section that is located laterally outwardly of the side surface of said package shell; and
an array shell separate from said package shells and said array substrate is disposed over said array shell and the perimeter section of said package substrate of said at least one EAP; and
a frame is embedded in said array shell, said frame having first and second opposed surfaces such that the package substrate of said at least one EAP is located outwardly of the first surface of said frame and said electrode of said at least one EAP is located outwardly of the second surface of said frame.

10. The electrode array of claim 1, wherein said components of said integrated circuit of each of said EAPs comprise:
a current source configured to source current through said electrode;
a current sink configured to sink current from said electrode; and
a state machine configured to control an on/off state of said current source and said current sink and configured to control a level of current for said current source and said current sink.

11. An electrode array for application against living tissue, said electrode array including:
a plurality of electrode ASIC packages (EAPs) arranged in an array, each of said plurality of EAPs including:
an integrated circuit having opposed top and bottom surfaces, said integrated circuit containing components configured to at least one of: source current through an electrode; sink current from an electrode; or measure a potential at an electrode; and with said integrated circuit including and at least one bond pad disposed on the bottom surface for establishing a conductive path to said components of said integrated circuit;
a package substrate formed from electrically insulating material, said package substrate having first and second opposed surfaces and wherein the bottom surface of said integrated circuit is mounted to the first surface of said package substrate, said package substrate including at least one conductive member that is electrically connected to said at least one bond pad of said integrated circuit;
a package shell formed from electrically insulating material disposed over the top surface of said integrated circuit wherein said package shell is formed with at least one side that extends between the top and bottom surfaces of said integrated circuit and said package shell and said package substrate are collectively dimensioned so that said package substrate has a perimeter section that extends laterally outwardly from the at least one side of said package shell; and
at least one electrode secured over said package shell so as to be disposed over the top surface of said integrated circuit and be rigidly integral with said integrated circuit, said at least one electrode being formed from material that can be placed in contact with living tissue and through which current sourced to or sunk from the living tissue wherein, said at least one electrode is electrically connected to the components of said integrated circuit; and an array substrate separate from said package substrates wherein the second surfaces of said package substrates of said plurality of EAPs are mounted to a first outer surface of said array substrate and said array substrate is formed from flexible, biocompatible material that is more flexible than said package substrates;

at least one electrically conductive array conductor mounted to said array substrate over which signals are at least one transmitted to or received from said components of said integrated circuits, said at least one array conductor being connected to said conductive members of said package substrates so that a conductive path is established through said at least one array conductor, said conductive members of said package substrates and said bond pads of said integrated circuits to the components of said integrated circuits; and an array shell separate from said array substrate and said package shells of said plurality of EAPs, said array shell being formed from flexible material and disposed over the first outer surface of said array substrate and the perimeter sections of said package substrates to hold at least two EAPs of said plurality to said array substrate.

12. The electrode array of claim 11, wherein at least one of said EAPs is further formed so to have a package electrode that extends over the at least one side of said package shell that extends over said integrated circuit and that provides an electrical connection between said components of said integrated circuit of said EAP and said at least one electrode of said EAP.

13. The electrode array of claim 11, wherein, at least one of said EAPs is further formed so that:
said integrated circuit of said EAP has plural bond pads;
a substrate conductor is disposed in said package substrate of said EAP so as to extend from one of said bond pads of said integrated circuit mounted to the perimeter section of said package substrate; and
a package electrode extends from an end of said substrate conductor disposed in the perimeter section of said package substrate to said at least one electrode of said EAP to provide an electrical connection between said components of said integrated circuit and said electrode.

14. The electrode array of claim 11, wherein:
said array substrate has a second outer surface opposite the first outer surface of said array substrate; and
said array shell is disposed over the second surface of said array substrate.

15. The electrode array of claim 11, wherein:
a frame is embedded in said array shell, said frame being more rigid than said array shell, and said frame is spaced from said at least two EAPs; and
portions of said array shell are disposed between said frame and said at least two EAPs.

16. The electrode array of claim 11, wherein:
a frame is embedded in said array shell, said frame being formed from material that is more rigid than said array shell and said frame is formed with windows;
said at least two of said EAPs and said frame are positioned so that at least two EAPs are seated in the windows of said frame, and said at least two EAPs and said frame are collectively dimensioned so that said at least two EAPs are spaced inwardly from surfaces of said frame that define perimeters of said windows; and portions of said array shell are disposed around said at least two EAPs so as to extend between said at least two EAPs and said frame.

17. An electrode array for application against living tissue, said electrode array including:
a plurality of electrode ASIC packages (EAPs) arranged in an array, each of said plurality of EAPs including:
an integrated circuit having opposed top and bottom surfaces, said integrated circuit containing components configured to at least one of: source current through an electrode; sink current from an electrode; or measure a potential at an electrode; and with said integrated circuit including at least first and second bond pads disposed on the bottom surface for establishing a conductive path to said components of said integrated circuit;
an electrically insulating package shell disposed over at least the top surface of said integrated circuit;
at least one electrode disposed over the portion of said package shell disposed over the top surface of said integrated circuit so that said at least one electrode is rigidly integral with said integrated circuit, said electrode being formed from material that can be placed in contact with living tissue and through which current can be sourced to or sunk from living tissue wherein, said at least one electrode is electrically connected to the components of said integrated circuit; and
a package substrate formed from electrically insulating material, wherein the bottom surface of said integrated circuit is mounted to said package substrate and said package substrate contains therein at least first and second package conductors, said first package conductor being connected to said first bond pad and said second package conductor being connected to said second bond pad;
an array substrate formed from flexible material so that said array substrate is more flexible than said package substrates of said plurality of EAPs, said array substrate having a first outer surface wherein said package substrates of said plurality of EAPs are mounted to the first outer surface of said array substrate;
at least one array conductor disposed within said array substrate over which signals are at least one of transmitted to or received from said integrated circuits of said plurality of EAPs, said at least one array conductor being connected to said first package conductors of said package substrates so that a conductive path is established through said at least one array conductor, said first package conductors and said first bond pads of said bond pads of said integrated circuits to the components of said integrated circuits;
an array shell disposed around said plurality of EAPs and over the first outer surface of said array substrate, said array shell being formed from material that is electrically insulating and more flexible than said array substrate; and
electrode conductors, said electrode conductors extending from said second package conductors, across said integrated circuits towards the top surfaces of the integrated circuits so that said second bond pads, said second package conductors and said electrode conductors provide a conductive path from the components of said integrated circuits to said electrodes.

18. The electrode array of claim 17, wherein at least one of said EAPs of said plurality is further formed so that:

said integrated circuit of said EAP has at least one side surface that extends between the bottom and top surfaces of said integrated circuit; and
said package shell of said EAP extends over the at least one side surface of said integrated circuit; and
said electrode conductor that is associated with said EAP extends between said integrated circuit of said EAP and said electrode of said EAP extends over the portion of said package shell that extends over the at least one side surface of said integrated circuit.

19. The electrode array of claim 17, wherein at least one of said EAPs of said plurality is further formed so that:
an electrically conductive trace is disposed in said package substrate and said conductive trace extends from said integrated circuit mounted of said EAP; and
an electrode conductor extends between said conductive trace disposed in said package substrate of said EAP and said electrode to provide an electrically conductive connection between said integrated circuit and said at least one electrode of said EAP.

20. The electrode array of claim 17, wherein at least one of said EAPs of said plurality is further formed so that:
said package shell of said EAP has a side surface that extends between the top and bottom surfaces of said integrated circuit of said EAP;
said package substrate of the at least one said EAP has a perimeter section that is located laterally outwardly of the side surface of said package shell; and
said array shell is disposed over the perimeter section of said package substrate.

21. The electrode array of claim 17, wherein at least one of said EAPs of said plurality is formed so that:
said package shell of said EAP has a side surface that extends between the top and bottom surfaces of said integrated circuit of said EAP;
said package substrate has a perimeter section that is located laterally outwardly of the side surface of said package shell;
said array shell is disposed over the perimeter section of said package substrate; and
internal to the package substrate is an electrically conductive trace that extends from said integrated circuit mounted to said package substrate to the perimeter section of said package substrate; and wherein, said electrode conductor associated with the integrated circuit of said EAP extends from the at least one said electrode of said EAP, through said array shell to the perimeter section of said package substrate and is connected to an end of said conductive trace within the perimeter section of said package substrate.

22. The electrode array of claim 17, wherein:
a frame is embedded in said array shell, said frame being more rigid than said array shell, and said frame is spaced from at least two EAPs of said plurality; and
portions of said array shell are disposed between said frame and said at least two EAPs.

23. The electrode array of claim 17, wherein:
a frame is embedded in said array shell, said frame being formed from material that is more rigid than said array shell and said frame being formed with windows;
at least two EAPs of said plurality and said frame are positioned so that said at least two EAPs are seated in the windows of said frame, and said at least two EAPs and said frame are collectively dimensioned so that said at least two EAPs are spaced inwardly from surfaces of said frame that define perimeters of said windows; and
portions of said array shell are disposed around said at least two EAPs so as to extend between said at least two EAPs and said frame.

24. The electrode array of claim 17, wherein:
at least one of said EAPs has a package shell with a side surface that extends between the top and bottom surfaces of said integrated circuit of said at least one EAP and said package substrate of said at least one EAP has a perimeter section that is located laterally outwardly of the side surface of said package shell; and
said array shell is separate from said package shells and said array substrate is disposed over said array shell and the perimeter section of said package substrate of said at least one EAP; and
a frame is embedded in said array shell, said frame having first and second opposed surfaces such that the package substrate of said at least one EAP is located outwardly of the first surface of said frame and said electrode of said at least one EAP is located outwardly of the second surface of said frame.

* * * * *